(12) United States Patent
Adler et al.

(10) Patent No.: US 7,294,613 B2
(45) Date of Patent: Nov. 13, 2007

(54) BETA-DEFENSINS

(75) Inventors: David A. Adler, Bainbridge Island, WA (US); James L. Holloway, Seattle, WA (US); Nand Baindur, Longmont, CO (US); Stephanie Beigel-Orme, Seattle, WA (US); Paul O. Sheppard, Granite Falls, WA (US)

(73) Assignee: ZymoGenetics, Inc., Seattle, WA (US)

( * ) Notice: Subject to any disclaimer, the term of this patent is extended or adjusted under 35 U.S.C. 154(b) by 830 days.

(21) Appl. No.: 10/091,166

(22) Filed: Mar. 5, 2002

(65) Prior Publication Data
US 2003/0143671 A1 Jul. 31, 2003

Related U.S. Application Data

(60) Division of application No. 09/636,399, filed on Aug. 10, 2000, now Pat. No. 6,576,755, which is a continuation-in-part of application No. 09/344,097, filed on Jun. 25, 1999, now abandoned, which is a continuation-in-part of application No. 09/150,786, filed on Sep. 10, 1998, now abandoned.

(60) Provisional application No. 60/064,294, filed on Nov. 5, 1997, provisional application No. 60/058,335, filed on Sep. 10, 1997.

(51) Int. Cl.
*A61K 38/00* (2006.01)
*C07K 14/00* (2006.01)

(52) U.S. Cl. .............................. 514/2; 514/12; 530/300; 424/9.1; 435/69.1; 536/23.2

(58) Field of Classification Search ................ 530/324, 530/300; 514/2, 9, 12; 424/9.1; 536/23.2; 435/69.1
See application file for complete search history.

(56) References Cited

U.S. PATENT DOCUMENTS 6,809,181 B2 * 10/2004 McCray et al. ............. 530/350

FOREIGN PATENT DOCUMENTS

| WO | 95/32287 | 11/1995 |
|---|---|---|
| WO | 99/06554 | 2/1999 |
| WO | 00/07612 | 2/2000 |
| WO | 01/42467 | 6/2000 |
| WO | 00/46245 | 8/2000 |
| WO | 02/04487 | 1/2002 |
| WO | 02/40512 | 5/2002 |

OTHER PUBLICATIONS

Jia et al., "Discovery of new human beta-defensins using a genomics-based approach," *Gene*, 263(1-2):211-218 (Jan. 2001).
Lehrer et al. "Defensins: antimicrobial and cytotoxic peptides of mammalian cells," *Annu Rev Immunol.*, 11:105-128 (1993). Review.
Harder et al. "A peptide antibiotic from human skin," *Nature*, 387(6636):861 (Jun. 26, 1997).
Incyte Pharmaceuticals, Inc. clone, 1996:INC1433022.
Incyte Pharmaceuticals, Inc. LIBRARY, 1996:BEPINON01.
Incyte Pharmaceuticals, Inc. LIBRARY, 1996: LPARNOT02.
Selsted et al., "Purification, primary structures, and antibacterial activities of beta-defensins, a new family of antimicrobial peptides from bovine neutrophils," *J Biol Chem.*, 268(9):6641-6648 (Mar. 25, 1993).
Bensch et al., "hBD-1: a novel beta-defensin from human plasma," *FEBS Lett.*, 368(2):331-335 (Jul. 17, 1995).
Bowie et al., "Deciphering the message in protein sequences: tolerance to amino acid substitutions," *Science*, 247(4948):1306-1310 (Mar. 16, 1990).
Wells, J.A., "Additivity of mutational effects in proteins," *Biochemistry*, 29(37):8509-8517 (Sep. 18, 1990).
Liu et al., "Structure and mapping of the human beta-defensin HBD-2 gene and its expression at sites of inflammation," *Gene*, 222(2):237-244 (Nov. 19, 1998).
Porter et al., "Broad-spectrum antimicrobial activity of human intestinal defensin 5," *Infect Immun.*, 65(6):2396-2401 (Jun. 1997).
Daher et al., "Direct inactivation of viruses by human granulocyte defensins," *J Virol.*, 60(3):1068-1074 (Dec. 1986).
Martin et al., "Defensins and other endogenous peptide antibiotics of vertebrates," *J Leukoc Biol.*, 58(2):128-136 (Aug. 1995). Review.
Ouellette et al., "Paneth cell defensins: endogenous peptide components of intestinal host defense," *FASEB J.*, 10(11):1280-1289 (Sep. 1996). Review.
Lichtenstein et al., "In vitro tumor cell cytolysis mediated by peptide defensins of human and rabbit granulocytes," *Blood*, 68(6):1407-1410 (Dec. 1986).

(Continued)

*Primary Examiner*—Chih-Min Kam
(74) *Attorney, Agent, or Firm*—Brian J. Walsh

(57) ABSTRACT

The present invention relates to polynucleotide and polypeptide molecules for zamp1, a novel member of the β-defensin family. The polypeptides, and polynucleotides encoding them, exhibit anti-microbial activity and may be used in the study or treatment of microbial infections. The present invention also includes antibodies to the zamp1 polypeptides.

10 Claims, 2 Drawing Sheets

OTHER PUBLICATIONS

Zhu et al., "Isolation and structure of corticostatin peptides from rabbit fetal and adult lung," *Proc Natl Acad Sci U S A.*, 85(2):592-596 (Jan. 1988).

Territo et al., "Monocyte-chemotactic activity of defensins from human neutrophils," *J Clin Invest.*, 84(6):2017-2020 (Dec. 1989).

Tamura et al., "A marked decrease in defensin mRNA in the only case of congenital neutrophil-specific granule deficiency reported in Japan," *Int J Hermatol.*, 59(2):137-142 (Feb. 1994).

Higazi et al., "Defensin modulates tissue-type plasminogen activator and plasminogen binding to fibrin and endothelial cells," *J Biol Chem.*, 271(30):17650-5 (Jul. 26, 1996).

Yang et al., "Mammalian defensins in immunity: more than just microbicidal," *Trends Immunol.*, 23(6):291-6 (Jun. 2002).

Cicro et al., "Structural and functional characterization of hBD-1(Ser35), a peptide deduced from a DEFB1 polymorphism," *Biochem Biophys Res Commun.*, 293(1):586-92 (Apr. 26, 2002).

Schibli et al., "The solution structures of the human beta-defensins lead to a better understanding of the potent bactericidal activity of HBD3 against *Staphylococcus aureus*," *J Biol Chem.*, 277(10):8279-89 (Mar. 8, 2002).

Harder et al., "Isolation and characterization of human beta - defensin-3, a novel human inducible peptide antibiotic," *J Biol Chem.*, 276(8):5707-13 (Feb. 23, 2001).

Goldman et al., "Human beta-defensin-1 is a salt-sensitive antibiotic in lung that is inactivated in cystic fibrosis," *Cell*, 88(4):553-60 (Feb. 21, 1997).

Smith et al., "Cystic fibrosis airway epthelia fail to kill bacteria because of abnormal airway surface fluid," *Cell*, 85(2):229-36 (Apr. 19, 1996).

Davies et al., "CFTR gene transfer reduces the binding of *Pseudomonas aeruginosa* to cystic fibrosis respiratory epithelium," *Am J Respir Cell Mol Biol.*, 16(6):657-63 (Jun. 1997).

Dunsche et al., "The novel human beta-defensin-3 is widely expressed in oral tissues," *Eur. J. Oral. Sci.*, 109:121-124 (2002).

Cullor et al., "In vitro antimicrobial activity of defensins against ocular pathogens," *Arch Ophthalmol.*, 108(6):861-864 (Jun. 1990).

Schwab et al., "Corneal storage medium preservation with defensins," *Cornea*, 11(5):370-375 (Sep. 1992).

Yeh et al., "Single-dose pharmacokinetics of indinavir and the effect of food," *Antimicrob Agents Chemother.*, 42(2):332-338 (Feb. 1998).

Haynes et al., "Innate defence of the eye by antimicrobial defensin peptides," *Lancet*, 352(9126):451-452 (Aug. 8, 1998).

Haynes et al., "Antimicrobial defensin peptides of the human ocular surface," *Br J Ophthalmol.*, 83(6):737-41 (Jun. 1999).

Sawicki et al., "Contraceptive potential of peptide antibiotics," *Lancet*, 353(9151):464-5 (Feb. 6, 1999).

Garcia et al., "Identification of a novel, multifunctional beta-defensin (human beta-defensin 3) with specific antimicrobial activity. Its interaction with plasma membranes of *Xenopus* oocytes and the induction of macrophage chemoattraction," *Cell Tissue Res.*, 306(2):257-64 (Nov. 2001).

Zasloff, M., "Antimicrobial peptides of multicellular organisms," *Nature*, 415:389-395 (Jan. 2002).

Krisanaprakomkit et al., "Regulation of human beta-defensin-2 in gingival epithelial cells: the involvement of mitogen-activated protein kinase pathways, but not the NF-kappaB transcription factor family," *J Immunol.*, 168(1):316-324 (Jan 1, 2002).

Garcia et al., "Human beta-defensin 4: a novel inducible peptide with a specific salt-sensitive spectrum of antimicrobial activity," *FASEB J.*, express article 10.1096/fj.00-0865fje, published online on Jun. 18, 2001.

Duits et al., "Inhibition of hBD-3, but not hBD-1 and hBD-2, mRNA expression by corticosteroids,"*Biochem Biophys Res Commun.*, 280(2):522-525 (Jan. 2001).

Hancock et al., "Antibiotic resistance in *Pseudomonas aeruginosa*: mechanisms and impact on treatment," *Drug Resist Updat.*, 3(4):247-255 (Aug. 2000).

Biragyn et al., "DNA vaccines encoding human immunodeficiency virus-1 glycoprotein 120 fusions with proinflammatory chemoattractants induced systemic and mucosal immune responses," *Blood*, 100(4):1153-1159 (Aug. 15, 2002).

\* cited by examiner

```
  0         .    :    .    :    .    :    .    :    .    :    .    :
  7  TATCTTCTGTTTGCTTTGCTCTTCCTGTTTTTGGTGCCTGTTCCAGGT    CATGGAGGA
     ::::::::::::  ....  ::::::  .  ::::::  ..:::  ..:::::::---  .:::::::
 12  Y   L   L   F   S   F   L   F   I   F   L   M   P   L   P   G   V   F   G   G

60         .    :    .    :    .    :    .    :    .    :    .    :
 64  ATCATAAACACATTACAGAAATAANATTGCAGAGTCAGAGGCGGCCGGTGTGCTGTGCTC
     :::  .  ..  ..  ..  .-----------:::  .  ..  :::..  :::  .  . ..
 32  I   G   D   P   V   T           C   L   K   S   G   A   I   C   H   P   V

120         .    :    .    :    .    :    .    :    .    :    .    :
124  AGCTGCCTTCCAAAGGAGGAACAGATCGGCAAGTGCTCGACGCGTGGCCGAAAATGCTGC
     .:::.  ..  ..  .  .  ..:::::::::.  .:::  .  ..  .:::  .:::::::::::
 49  F   C   P   R   R   Y   K   Q   I   G   T   C   G   L   P   G   T   K   C   C

180       .
184  CGAAGA
     ...  .
 69  K   K
```

Fig. 2

BETA-DEFENSINS

REFERENCE TO RELATED APPLICATIONS

The present application is a divisional application of U.S. patent application Ser. No. 09/636,399, filed Aug. 10, 2000, now U.S. Pat. No. 6,576,755, which is a continuation-in-part of U.S. patent application Ser. No. 09/344,097, filed on Jun. 25, 1999, now abandoned, which is a continuation-in-part of U.S. patent application Ser. No. 09/150,786, filed on Sep. 10, 1998, now abandoned, which is related to Provisional Applications 60/058,335, filed on Sep. 10, 1997 and 60/064,294, filed on Nov. 5, 1997, all of which are herein incorporated by reference. Under 35 U.S.C. § 119(e)(1), this application claims benefit of said Provisional Applications.

BACKGROUND OF THE INVENTION

Biological defense strategies have evolved to protect organisms from invasion by other species. Microbial infection response systems include oxidative and non-oxidative mechanisms, utilizing compounds that are enzymatically synthesized in cells and peptides that are single gene products.

Anti-microbial peptides constitute an oxygen-independent host defense system found in organisms encompassing many taxonomic families. One major class of anti-microbial peptides can be sequence-defined by conserved cysteine residue patterns and are termed defensins. Mammalian defensins, derived from skin, lung and intestine, exhibit antibiotic activity against a wide variety of pathogens, including gram-positive and gram-negative bacteria, fungi (e.g. *Candida* species) and viruses. See, for example, Porter et al., *Infect. Immun.* 65(6): 2396-401, 1997.

The amphipathic character of the defensin peptides appears to be the key to the general mechanism of microbial attack, i.e., by creating pores, or "boring" through the cell wall. In addition, Daher et al., *J. Virol.* 60(3): 1068-74, 1986, reported that enveloped viruses, including herpes simplex types 1 and 2, cytomegalovirus and influenza virus (A/WSN), among others, were inactivated by incubation with human neutrophil peptide (HNP-1) and speculated that the binding of defensin molecules to viruses impairs the virus' ability to infect cells.

The defensin family of anti-microbial peptides can be divided into two major subclasses based on two distinct consensus sequences. See, for example, Martin et al., *Journal of Leukocyte Biology* 58: 128-36, 1995. The first defensin subclass, classic defensins, represented by HNPs are stored in the so-called large azurophil granules of neutrophils and macrophages and attack microorganisms that have been phagocytosed by these cells. The amino acid sequence of HNPs is consistent with a predicted disulfide bridging that is distinct from that of the β-defensin subclass. Epithelial cells can also be a source of defensins, and these cells appear to secrete these peptides into the external, extra-cellular environment. In the mouse, for example, Paneth cells of the small intestine and proximal colon, secrete defensin-like peptides, called cryptidins, into the lumen. See, for example, Ouellette and Selsted, *The FASEB Journal* 10: 1280-9, 1996.

β-defensins, the second major defensin subclass, include peptides found in bovine lung (e.g., BNBD-bovine neutrophil β-defensins) as well as a secreted form (TAP—tracheal anti-microbial peptide). See, for example, Selsted et al., *J. Biol. Chem.* 268(9): 6641-8, 1993. Two human β-defensins have been reported. SAP-1 was isolated from human psoriatic skin, and hBD-1 was found in low concentrations in human blood filtrate. See, for example, Bensch et al., *FEBS Lett.* 368(2): 331-5, 1995). The amino acid sequence of these human β-defensins is most similar to the bovine BNDPs and TAP. See, for example, Harder et al., *Nature* 387: 861, 1997, wherein SAP-1 is designated hBD-2.

Other than the conserved cysteine residues the defensin family is quite sequence divergent. It is possible that the variant amino acid positions may be related to the site or conditions of activity or to the spectrum of pathogens attacked by a particular defensin.

In addition to anti-microbial activities, particular defensins exhibit metabolically sensitive cytotoxic activity (Lichtenstein et al., *Blood* 68: 1407-10, 1986 and Sheu et al., *Antimicrob. Agents Chemother.* 28: 626-9, 1993), alter the response of adrenal cortical cells to ACTH (Zhu et al., *Proc. Natl. Acad. Sci. (USA)* 85(2): 592-6, 1988) and have specific chemotactic activity for human monocytes (Territo et al., *J. Clin. Invest.* 84(6): 2017-20, 1989). Recruitment of monocytes by neutrophils may, in part, be mediated by neutrophilic defensins and suggests a pro-inflammatory activity for these peptides in addition to their anti-microbial effects. Also, a decrease in defensin mRNA level has been demonstrated in SPG (specific granule disease). See, for example, Tamura et al., *Japan. Int. J. Hematol.* 59(2): 137-42, 1994. Higazi et al., *J. Biol. Chem.* 271(3): 17650-5, 1996, suggested that plasminogen bound to fibrin in the presence of defensin may be less susceptible to activation by tPA.

Moieties having anti-microbial, immunostimulatory, pro-inflammatory and other properties of defensins are sought. The present invention provides such polypeptides for these and other uses that should be apparent to those skilled in the art from the teachings herein.

SUMMARY OF THE INVENTION

Within one aspect the invention provides an isolated protein comprising a polypeptide that is at least 80% identical to a polypeptide selected from the group consisting of: a) a polypeptide having the sequence of amino acid residue 1 to amino acid residue 65 of SEQ ID NO:2; b) a polypeptide having the sequence of amino acid residue 19 to amino acid residue 65 of SEQ ID NO:2; c) a polypeptide having the sequence of amino acid residue 21 to amino acid residue 65 of SEQ ID NO:2; d) a polypeptide having the sequence of amino acid residue 1 to amino acid residue 67 of SEQ ID NO:10; e) a polypeptide having the sequence of amino acid residue 21 to amino acid residue 67 of SEQ ID NO:10; and f) a polypeptide having the sequence of amino acid residue 23 to amino acid residue 67 of SEQ ID NO:10; wherein the polypeptide has cysteine residues corresponding to amino acid residues 33, 40, 45, 55, 62 and 63 of SEQ ID NOs:2 or 10. Within one embodiment the protein comprises a polypeptide having the sequence selected from the group consisting of: a) a polypeptide having the sequence of amino acid residue 1 to amino acid residue 67 of SEQ ID NO:10; b) a polypeptide having the sequence of amino acid residue 21 to amino acid residue 67 of SEQ ID NO:10; and c) a polypeptide having the sequence of amino acid residue 23 to amino acid residue 67 of SEQ ID NO:10.

Within another aspect is provided an isolated protein having the sequence of SEQ ID NO:10 from amino acid residue 23 to amino acid residue 67.

Within another aspect the invention provides a polypeptide selected from the group consisting of: a) amino acid residue 30 to amino acid residue 63 of SEQ ID NO:2; b) amino acid residue 31 to amino acid residue 63 of SEQ ID NO:2; c) amino acid residue 30 to amino acid residue 64 of SEQ ID NO:2; d) amino acid residue 31 to amino acid residue 64 of SEQ ID NO:2; and e) a polypeptide chosen from SEQ ID NOs:14-72.

Within still another aspect is provided a pharmaceutical composition comprising a polypeptide selected from the group consisting of: a) a protein according to claim 1, b) amino acid residue 30 to amino acid residue 63 of SEQ ID NO:2; c) amino acid residue 31 to amino acid residue 63 of SEQ ID NO:2; d) amino acid residue 30 to amino acid residue 64 of SEQ ID NO:2; e) amino acid residue 31 to amino acid residue 64 of SEQ ID NO:2; and f) a polypeptide chosen from SEQ ID NOs:14-72; in combination with a pharmaceutically acceptable vehicle.

Within yet another aspect is provided an antibody that specifically binds to a protein as described above.

Within a further aspect is provided an anti-idiotypic antibody of an antibody which specifically binds to a protein as described above.

Within another aspect is provided an isolated polynucleotide molecule encoding a protein, the polynucleotide molecule consisting of a coding strand and a complementary non-coding strand, wherein the polynucleotide molecule encodes a polypeptide that is at least 80% identical to the amino acid sequence to a polypeptide selected from the group consisting of: a) a polypeptide having the sequence of amino acid residue 1 to amino acid residue 65 of SEQ ID NO:2; b) a polypeptide having the sequence of amino acid residue 19 to amino acid residue 65 of SEQ ID NO:2; c) a polypeptide having the sequence of amino acid residue 21 to amino acid residue 65 of SEQ ID NO:2; d) a polypeptide having the sequence of amino acid residue 1 to amino acid residue 67 of SEQ ID NO:10; e) a polypeptide having the sequence of amino acid residue 21 to amino acid residue 67 of SEQ ID NO:10; and f) a polypeptide having the sequence of amino acid residue 23 to amino acid residue 67 of SEQ ID NO:10; wherein the polypeptide has cysteine residues corresponding to amino acid residues 33, 40, 45, 55, 62 and 63 of SEQ ID NOs:2 or 10.

Within another aspect the invention provides an isolated polynucleotide molecule encoding a protein having cysteine residues corresponding to amino acid residues 33, 40, 45, 55, 62 and 63 of SEQ ID NO:10, the polynucleotide molecule consisting of a coding strand and a complementary non-coding strand, wherein the polynucleotide comprises a nucleotide sequence that is at least 80% identical to the sequence of a polynucleotide selected from the group consisting of: a) a polynucleotide as shown in SEQ ID NO:9 from nucleotide 220 to nucleotide 420; b) a polynucleotide as shown in SEQ ID NO:9 from nucleotide 280 to nucleotide 420; and c) a polynucleotide as shown in SEQ ID NO:9 from nucleotide 286 to nucleotide 420.

Within yet another aspect is provided an isolated polynucleotide molecule encoding a protein having cysteine residues corresponding to amino acid residues 33, 40, 45, 55, 62 and 63 of SEQ ID NO:10, the polynucleotide molecule consisting of a coding strand and a complementary non-coding strand, wherein the polynucleotide comprises a nucleotide sequence as shown in SEQ ID NO:11.

Within another aspect is provided an isolated polynucleotide molecule encoding a polypeptide selected from the group consisting of: a) amino acid residue 30 to amino acid residue 63 of SEQ ID NO:2; b) amino acid residue 31 to amino acid residue 63 of SEQ ID NO:2; c) amino acid residue 30 to amino acid residue 64 of SEQ ID NO:2; d) amino acid residue 31 to amino acid residue 64 of SEQ ID NO:2; and e) a polypeptide chosen from SEQ ID NOs:14-72.

The invention also provides an isolated polynucleotide molecule selected from the group consisting of:
a) nucleotide 88 to nucleotide 189 of SEQ ID NO:1;
b) nucleotide 88 to nucleotide 192 of SEQ ID NO:1;
c) nucleotide 91 to nucleotide 189 of SEQ ID NO:1;
d) nucleotide 91 to nucleotide 192 of SEQ ID NO:1;
e) nucleotide 88 to nucleotide 189 of SEQ ID NO:4;
f) nucleotide 88 to nucleotide 192 of SEQ ID NO:4;
g) nucleotide 91 to nucleotide 189 of SEQ ID NO:4 and
h) nucleotide 91 to nucleotide 192 of SEQ ID NO:4.

Within still another aspect is provided an expression vector comprising the following operably linked elements: a transcription promoter; a DNA segment encoding a polypeptide selected from the group consisting of: a) a protein of claim 1; a) amino acid residue 30 to amino acid residue 63 of SEQ ID NO:2; b) amino acid residue 31 to amino acid residue 63 of SEQ ID NO:2; c) amino acid residue 30 to amino acid residue 64 of SEQ ID NO:2; d) amino acid residue 31 to amino acid residue 64 of SEQ ID NO:2; and e) a polypeptide chosen from SEQ ID NOs:14-72; and a transcription terminator. Within one embodiment the DNA segment further encodes a secretory signal sequence operably linked to the protein. Within a related embodiment the secretory signal sequence is selected from the group consisting of: a) a polypeptide having the sequence of amino acid residue 1 to amino acid residue 18 of SEQ ID NO:2; b) a polypeptide having the sequence of amino acid residue 1 to amino acid residue 20 of SEQ ID NO:2; c) a polypeptide having the sequence of amino acid residue 1 to amino acid residue 20 of SEQ ID NO:10; and d) a polypeptide having the sequence of amino acid residue 1 to amino acid residue 22 of SEQ ID NO:10.

Within another aspect the invention provides a cultured cell into which has been introduced an expression vector comprising the following operably linked elements: a transcription promoter; a DNA segment encoding a polypeptide as described above; and a transcription terminator; wherein the cell expresses the protein encoded by the DNA segment.

Within a further aspect is provided a method of producing a protein comprising: culturing a cell into which has been introduced an expression vector comprising the following operably linked elements: a transcription promoter; a DNA segment encoding a polypeptide as described above; and a transcription terminator; whereby the cell expresses the protein encoded by the DNA segment; and recovering the expressed protein.

The invention also provides an oligonucleotide probe or primer comprising at least 14 contiguous nucleotides of a polynucleotide of SEQ ID NO:11 or a sequence complementary to SEQ ID NO:11.

The invention further provides a method of treating a microbial-related disease comprising administering to a mammal a therapeutically effective amount of a polypeptide selected from the group consisting of: a) a polypeptide of SEQ ID NO:2; b) a polypeptide of SEQ ID NO:10; c) a polypeptide chosen from SEQ ID NOs:14-72; h) amino acid residue 30 to amino acid residue 63 of SEQ ID NO:2; i) amino acid residue 31 to amino acid residue 63 of SEQ ID NO:2; j) amino acid residue 30 to amino acid residue 64 of SEQ ID NO:2; k) amino acid residue 31 to amino acid residue 64 of SEQ ID NO:2; l) amino acid residue 20 to amino acid residue 67 of SEQ ID NO:10 and m) amino acid residue 22 to amino acid residue 67 of SEQ ID NO:10; whereby said polypeptide ameliorates said disease. Within one embodiment the microbial-related disease is associated with the eye. Within a related embodiment the microbial-related disease is conjunctivitis. Within another embodiment the microbial-related disease is associated with the ear.

Also provided is a method of contraception comprising administering to a mammal a therapeutically effective amount of a polypeptide selected from the group consisting of: a) a polypeptide of SEQ ID NO:2; b) a polypeptide of SEQ ID NO:10; c) a polypeptide chosen from SEQ ID NOs:14-72; h) amino acid residue 30 to amino acid residue 63 of SEQ ID NO:2; i) amino acid residue 31 to amino acid residue 63 of SEQ ID NO:2; j) amino acid residue 30 to amino acid residue 64 of SEQ ID NO:2; k) amino acid residue 31 to amino acid residue 64 of SEQ ID NO:2; l) amino acid residue 20 to amino acid residue 67 of SEQ ID NO:10 and m) amino acid residue 22 to amino acid residue 67 of SEQ ID NO:10.

BRIEF DESCRIPTION OF THE DRAWINGS

FIG. 2 illustrates a multiple alignment of mature, processed human SAP-1 (see, for example, Bensch et al., *FEBS Lett.* 368(2): 331-5, 1995) and the zamp1 polypeptide of the present invention.

DETAILED DESCRIPTION OF THE INVENTION

Figure 1:
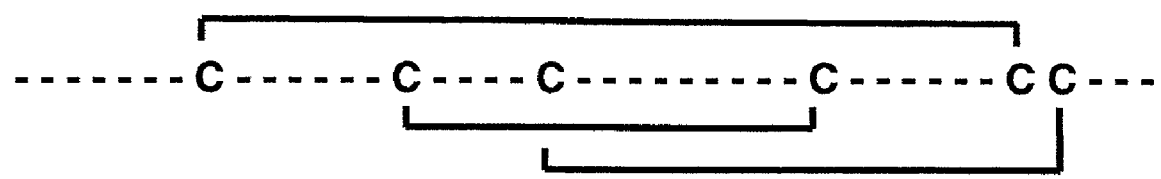
FIG. 1 illustrates the three disulfide bond structure of the conserved β-defensin motif.

Prior to setting forth the invention in detail, it may be helpful to the understanding thereof to define the following terms.

The term "affinity tag" is used herein to denote a peptide segment that can be attached to a polypeptide to provide for purification of the polypeptide or provide sites for attachment of the polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), substance P, Flag™ peptide (Hopp et al., *Biotechnology* 6:1204-1210, 1988; available from Eastman Kodak Co., New Haven, Conn.), streptavidin binding peptide, or other antigenic epitope or binding domain. See, in general Ford et al., *Protein Expression and Purification* 2: 95-107, 1991. DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

The term "ortholog" denotes a polypeptide or protein obtained from one species that is the functional counterpart of a polypeptide or protein from a different species. Sequence differences among orthologs are the result of speciation.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" denotes a portion of a gene containing DNA sequences that provide for the binding of RNA polymerase and initiation of transcription. Promoter sequences are commonly, but not always, found in the 5' non-coding regions of genes.

The term "receptor" denotes a cell-associated protein that binds to a bioactive molecule (i.e., a ligand) and mediates the effect of the ligand on the cell. membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a polypeptide having homology to proteins of the β-defensin family. That is, the zamp1 polypeptides of the present invention exhibit a conserved motif shown in SEQ ID NO: 3 and herein: $C(X)_6C(X)_4C(X)_7GXC(X)_6CC$ wherein "(X)" is the number of preferably non-cysteine amino acid residues between specific amino acids. The cysteine position and spacing is characteristic of the β-defensin family. In addition, the QIG tripeptide motif embedded in the conserved motif shown in SEQ ID NO:3 occurs in several members of the β-defensin family (for example, SAP-1/hBD-2, BNBDs, TAP and the like). This motif is interpreted to indicate the presence of three disulfide bonds in the β-defensin structure. Those disulfide bonds are shown in FIG. 1. In addition, an intron sequence of approximately 900 base pairs is found in genomic DNA sequence encoding the zamp1 polypeptide. This intron sequence is inserted between the two guanine residues in the codon encoding the glycine residue at amino acid position 20 in SEQ ID NO:10. Such intron placement, in the area between the signal sequence and the mature protein occurs in other members of the β-defensin family.

A standard Northern blot tissue distribution of the mRNA corresponding to this novel DNA revealed no expression. It thus appears that normal tissue levels of mRNA of zamp1 polypeptide are below the detection sensitivity of the Northern blot. Such an observation is consistent with the knowledge in the art regarding defensins, i.e., that they are constitutively expressed at low levels but are highly inducible upon infection. Electronic analysis of tissue distribution based upon libraries where the sequence is found indicate that zamp1 polypeptide is expressed in bronchial epithelia.

The novel zamp1 polypeptides of the present invention were initially identified by querying an EST database for homologous sequences to the SAP-1 human defensin isolated from human psoriatic skin. A single EST sequence was discovered in a bronchial epithelium cDNA library and was predicted to be related to the β-defensin family. A second search based upon the β-defensin consensus motif also identified the EST. Thus, the consensus motif is found in the zamp1 polypeptide as well as in the SAP-1 protein; however, the remaining sequence of the two proteins is divergent, characterized by approximately 43% identity at the amino acid level. See, for example, the multiple alignment shown in FIG. 2.

The nucleotide sequence of the zamp1 polypeptide is described in SEQ ID NO:1 and SEQ ID NO:9, and its deduced amino acid sequence is described in SEQ ID NO:2 and SEQ ID NO:10, respectively. The zamp1 polypeptide, by sequence analysis, can be grouped with the two human β-defensins, hBD-1 and hBD-2 (SAP-1), but it is most closely sequence-related to hBD-2 and the bovine BNBDs and less similar to hBD-1.

Preliminary computer-aided model building efforts to construct a three-dimensional model structure for zamp1 polypeptide indicate that it is feasible to generate physically reasonable model structures using BNBD_12 (Zimmermann et al., Biochemistry 34(41): 13663-13671, 1995) as a template. Although there is relatively low sequence identity between these two peptides, their overall secondary structure is very similar. The most variability is observed in the loop regions, which is not alarming since the loop segments represent one of many possible conformations for each loop. Both structures are built primarily of an anti-parallel beta sheet core, four-stranded in the BNBD_12 model and three-stranded in the zamp1 polypeptide model. A turn formed between two of the beta strands in the BNBD_12 chain is also found in the zamp1 polypeptide model connecting two beta strands. The overall folding of BNBD_12 follows the pattern of beta strand/short beta strand/short beta strand/turn/beta strand. Folding of zamp1 polypeptide consists of beta strand/beta strand/turn/beta strand. These common structural elements are highly superimposable. Thus, the two polypeptides may well be involved in the same or similar biological processes.

Another aspect of the present invention includes zamp1 polypeptide fragments. Preferred fragments include the leader sequence, ranging from amino acid 1 (Ile) to amino acid 18 (Gly) or 20 (Gly) of SEQ ID NO:2 and ranging from amino acid 1 (Met) to amino acid 20 (Gly) or 22 (Gly) of SEQ ID NO:10. Such leader sequences may be used to direct the secretion of other polypeptides. Such fragments of the present invention may be used as follows: the alternative secretion leader fragments are formed as fusion proteins with alternative proteins selected for secretion; plasmids bearing regulatory regions capable of directing the expression of the fusion protein are introduced into test cells; and secretion of the protein is monitored.

Additional preferred fragments include the β-hairpin loop of the zamp1 polypeptide, amino acid 30 (Lys) or 31 (Tyr) to amino acid 63 (Cys) or amino acid 64 (Arg) of SEQ ID NO:2, SEQ ID NO:14, and SEQ ID NOs:18-34. Also provided are the polypeptides of SEQ ID NO:15, SEQ ID NO:16, SEQ ID NO:17, SEQ,ID NOs:35-72, that eliminate the structural complications presented by the free cysteine residues (amino acids 55 and 62 of SEQ ID NO:2) and maintain the hydrophobic face of the polypeptide. The fragments provided by the invention would be useful in applications, described herein, where administration of zamp1 would be beneficial, such as anti-microbial agents (Thennarasu and Nagaraj, Biochem. Biophys. Res. Comm. 254:281-3, 1999).

The present invention also provides fusion constructs incorporating the zamp1 polypeptide selected from the group consisting of: (a) polypeptide molecules comprising a sequence of amino acid residues as shown in SEQ ID NO:2 from amino acid residue 1 (Ile), 19 (His) or 21 (Gly) to amino acid residue 65 (Lys) or a sequence of amino acid residues as shown in SEQ ID NO: 10 from amino acid residue 1 (Met), 21 (His) or 23 (Gly) to amino acid residue 67 (Lys); or (b) mammalian species homologs or human paralogs of (a); at least the mature polypeptide region of another defensin molecule; and, optionally, a polypeptide linker there between. When defensin molecules having disparate spectrum of pathogens, fusion constructs containing the same are expected to exhibit a broader range of anti-microbial effectiveness. Polypeptide linkers are preferably employed if necessary to provide separation of component polypeptides of the fusion or to allow for flexibility of the fusion protein, thereby preserving the anti-microbial activity of each defensin component of the fusion protein. Those of ordinary skill in the art are capable of designing such linkers.

The highly conserved amino acids in the consensus domain of zamp1 polypeptide can be used as a tool to identify new family members. For instance, reverse transcription-polymerase chain reaction (RT-PCR) can be used to amplify sequences encoding the conserved motif from RNA obtained from a variety of tissue sources. More specifically, the following probes can be employed to identify other human or zamp1-like β-defensins. A preferred embodiment of this aspect of the present invention ranges between amino acid residues 31 and 61 of SEQ ID NO: 2 (corresponding to nucleotides 91-183 of SEQ ID NO: 1). In particular, highly degenerate primers designed from the above sequences are useful for this purpose.

SEQ ID NO: 4 is a degenerate polynucleotide sequence that encompasses all polynucleotides that encode the zamp1 polypeptide of SEQ ID NO: 2 (amino acids 1-65). SEQ ID NO: 11 is a degenerate polynucleotide sequence that encompasses all polynucleotides that encode the zamp1 polypeptide of SEQ ID NO: 10. Thus, zamp1 polypeptide-encoding polynucleotides ranging from nucleotide 1, 61 or 67 to nucleotide 195 or 213 of SEQ ID NO: 4 and ranging from nucleotide 1, 61 or 67 to nucleotide 201 or 219 of SEQ ID NO: 11 are contemplated by the present invention. Also contemplated by the present invention are fragments and fusions as described above with respect to SEQ ID NO: 1 and SEQ ID NO: 10, which are formed from analogous regions of SEQ ID NO: 4 and SEQ ID NO: 11. The symbols in SEQ ID NO: 4 are summarized in Table 1 below.

TABLE 1

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | A\|T |
| W | A\|T | W | C\|G |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO: 4 and SEQ ID NO: 11, encompassing all possible codons for a given amino acid, are set forth in Table 2 below.

TABLE 2

| Amino Acid | Letter | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |

TABLE 2-continued

| Amino Acid | Letter | Codons | Degenerate Codon |
|---|---|---|---|
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |
| Gap | - | - - - | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY) A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO: 2 and SEQ ID NO: 10. Variant sequences can be readily tested for functionality as described herein.

Within another aspect of the present invention there is provided a pharmaceutical composition comprising purified zamp1 polypeptide in combination with a pharmaceutically acceptable vehicle. Such pharmaceutical compositions are used in the treatment of conditions associated with pathological microbes, including bacterial, fungal and viral infections. Antibacterial applications of zamp1 polypeptide include situations where the pathogen has become resistant to standard treatments. For example, hospital sepsis is an increasing problem, since *Staphylococcus* strains have become resistant to commonly used antibiotics.

In general, anti-microbial activity of zamp1 polypeptides, fragments, fusions, antibodies, agonists and antagonists can be evaluated by techniques that are known in the art. More specifically, anti-microbial activity can be assayed by evaluating the sensitivity of microbial cell cultures to test agents and by evaluating the protective effect of test agents on infected mice. See, for example, Musiek et al., *Antimicrob. Agents Chemothr.* 3: 40, 1973. Antiviral activity can also be assessed by protection of mammalian cell cultures. Known techniques for evaluating anti-microbial activity include, for example, Barsum et al., *Eur. Respir. J.* 8(5): 709-14, 1995; Sandovsky-Losica et al., *J. Med. Vet. Mycol (England)* 28(4): 279-87, 1990; Mehentee et al., *J. Gen. Microbiol (England)* 135 (Pt. 8): 2181-8, 1989; Segal and Savage, *Journal of Medical and Veterinary Mycology* 24: 477-479, 1986 and the like. Known assays specific for anti-viral activity include, for example, those described by Daher et al., *J. Virol.* 60(3): 1068-74, 1986.

In addition, contract laboratories offer services in evaluating anti-microbial properties. For example, Panlabs, Inc. of Bothell, Wash. offer in vitro or in vivo testing for bacteria, gram negative (*Enterobacter cloacae*, *Escherichia coli*, *Klebsiella pneumonia*, *Proteus vulgaris*, *Pseudomonas aeruginosa*, *Salmonella typhimurium* and *Serratia marcescens*), gram positive (*Bacillus subtilis*, *Brevebacterium ammoniagenes*, *Corynebacterium minutissimum*, *Micrococcus luteus*, *Mycobacterium ranae*, *Staphylococcus* strains and *Streptococcus* strains) and anaerobic organisms (*Actinomyces viscosus*, *Bacteroides fragilis*, *Clostridium sporogenes*, *Corynebacterium acnes*, *Helicobacter pylori* and *Porphyromonas gingivalis*), as well as for protozoa (*Trichomonas foetus*) and fungi (e.g., *Candida albicans*, *Epidermophyton floccosum*, *Exophiala jeanselmei*, *Microsporum* strains, *Trichophyton* strains and the like). Also, Molecular Probes of Oregon has commercially available fluorescence technology for use in bacteriology.

If desired, zamp1 polypeptide, fragment, fusion protein, agonist, antagonist or antibody performance in this regard can be compared to proteins known to be functional in this regard, such as proline-rich proteins, lysozyme, histatins, lactoperoxidase or the like. In addition, zamp1 polypeptide, fragment, fusion protein, antibody, agonist or antagonist may be evaluated in combination with one or more anti-microbial agents to identify synergistic effects.

Defensins have been found associated with the tissues and secretions of the human eye and are useful in treating microbial-related diseases of the eye (Cullor et al., *Arch. Ophthalmol.* 108:861-4, 1990; Murphy et al., U.S. Pat. No. 5,242,902; Hattenbach et al., *Antimicrob. Agent. Chemother.* 42:332, 1998; Haynes et al., *Lancet* 354:451-2, 1998 and Haynes et al., *Br. J. Ophthalmol.* 83:737-41, 1999). Addition of defensin polypeptides reduced microbial contamination of corneal preservation medium. Such agents are useful for reducing infectious postoperative complications associated with such transplantations (Schwab et al., *Cornea* 11:370-5, 1992).

Thus, zamp1 polypeptides, agonists or antagonists thereof may be therapeutically useful for treatment of infection and inflammation associated with the eye. To verify the presence of this capability in zamp1 polypeptides, agonists or antagonists of the present invention, such zamp1 polypeptides, agonists or antagonists are evaluated with respect to their anti-microbial and chemotactic activities according to procedures known in the art. If desired, zamp1 polypeptide performance in this regard can be compared to other α and β defensins, rabbit neutrophil defensins and the like. In addition, zamp1 polypeptides or agonists or antagonists thereof may be evaluated in combination with one or more anti-microbial molecules to identify synergistic effects.

Similarly, zamp1 polypeptides of the present invention would also be therapeutically useful for treatment of infection and inflammation associated with the ear. The invention provides a method of treating a microbial-related disease comprising administering to a mammal a therapeutically effective amount of a zamp1 polypeptide whereby the polypeptide ameliorates the disease. Preferably such polypeptides include the β-hairpin loop of the zamp1 polypeptide, amino acid 30 (Lys) or 31 (Tyr) to amino acid 63 (Cys) or amino acid 64 (Arg) of SEQ ID NO:2, SEQ ID NO:14 and SEQ ID NOs:18-34. Additional exemplary polypeptides include the polypeptides of SEQ ID NO:15, SEQ ID NO:16, SEQ ID NO:17 and SEQ ID NOs:35-72. One such application would be for microbial-related disease is associated with the eye, such as conjunctivitis. Application could also be made for diseases associated with the ear.

The invention also provides a method of contraception wherein a therapeutically effective amount of the polypeptides of the present invention is administered to a mammal. Such administration would be useful in preventing implantation and/or development of the embryo.

Defensins have also been found to activate the complement cascade (Proházska et al., *Mol Immunol.* 34:809-16, 1997 and Proházska and Füst, *Lancet* 352:1152, 1998) The complement component C1q plays a role in host defense against infectious agents, such as bacteria and viruses. C1q is known to exhibit several specialized functions. For example, C1q triggers the complement cascade via interaction with bound antibody or C-reactive protein (CRP). Also, C1q interacts directly with certain bacteria, RNA viruses, mycoplasma, uric acid crystals, the lipid A component of bacterial endotoxin and membranes of certain intracellular organelles. C1q binding to the C1q receptor is believed to promote phagocytosis. C1q also appears to enhance the antibody formation aspect of the host defense system. See, for example, Johnston, *Pediatr. Infect. Dis. J.* 12: 933-41, 1993. Thus, complement-activating defensins would act as enhanced anti-microbial agents, promoting lysis or phagocytosis of infectious agents.

The anti-microbial activity of defensins is also useful for contraceptive applications (Sawicki and Mystkovska, *Lancet* 353:464-5, 1999).

The pharmaceutical compositions of the present invention may also be used when pro-inflammatory activity is desired. Applications for such pro-inflammatory activity include the treatment of chronic tissue damage, particularly in areas having a limited or damaged vascular system, e.g., damage in extremities associated with diabetes. In contrast, antagonists to zamp1 polypeptides may be useful as anti-inflammatory agents.

Zamp1 polypeptide pharmaceutical compositions of the present invention may also be used in the treatment of conditions where stimulation of immune responsiveness is desired. Such conditions include the treatment of patients having incompetent immune systems, such as AIDs patients or individuals that have undergone chemotherapy, radiation treatment or the like.

Because zamp1 polypeptide was found in a bronchial epithelia library and cystic fibrosis is characterized by frequent microbial infection, pharmaceutical compositions containing zamp1 polypeptide are also contemplated for use in the treatment of lung infections associated with cystic fibrosis. Also contemplated by the present invention are engineered zamp1 polypeptides that are characterized by decreased sensitivity to salt concentration. Decreased sensitivity to high salt concentration will preserve anti-microbial activity of engineered zamp1 polypeptides in high salt environments, such as in the lung airways of patients suffering from cystic fibrosis. In this manner, pharmaceutical compositions containing engineered zamp1 polypeptides that are formulated for delivery to the lungs can be used to treat lung infections associated with cystic fibrosis.

Radiation hybrid mapping is a somatic cell genetic technique developed for constructing high-resolution, contiguous maps of mammalian chromosomes (Cox et al., *Science* 250:245-50, 1990). Partial or full knowledge of a gene's sequence allows one to design PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The results showed that the zampi gene maps 33.5 cR_3000 from the top of the human chromosome 8 linkage group on the WICGR radiation hybrid map. Proximal and distal framework markers were CHLC.GATA62D10 and WI-3823 (D8S1511), respectively. The use of surrounding markers positions the zampi gene in the 8p23.3-p23.2 region on the integrated LDB chromosome 8 map (located on the Internet, e.g. a public server of The Genetic Location Database, University of Southhampton.

Previously, human defensin genes of both hematopoietic (such as HD-1, as described by Sparkes et al., *Genomics* 5(2): 240-4, 1989) and epithelial (such as HD-5 and HD-6, as described by Bevins et al., *Genomics* 31(1): 95-106, 1996) origin are localized on the short arm of human chromosome 8 (8p23). Several defensin genes, cryptidins, have been mapped in the mouse genome and are found in a region of conserved synteny with human on mouse chromosome 8. See, for example, Ouellette et al., *Genomics* 5(2): 233-9, 1989. Recently, Liu et al., *Genomics* 43(3): 316-20, 1997, reported the mapping of the hBD_1 gene to the same cluster of defensins on chromosome 8. These authors propose that α- and β-defensin genes arose from a common ancestral gene prior to mammalian divergence. Thus, the localization of the zamp1 polypeptide-encoding gene to this region of chromosome 8 adds a second human β-defensin to the same chromosomal location as the human classic defensins and supports the hypothesis for the evolution of defensins.

The present invention also provides reagents which will find use in diagnostic applications. For example, the zamp1 gene, a probe comprising zamp1 DNA or RNA or a subsequence thereof can be used to determine if the zamp1 gene is present on chromosome 8 or if a mutation has occurred. Detectable chromosomal aberrations at the zamp1 gene locus include but are not limited to aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel, et. al., ibid.; Marian, *Chest*, 108: 255-265, 1995).

Another aspect of the present invention involves the detection of zamp1 polypeptides in cell culture or in a serum sample or tissue biopsy of a patient undergoing evaluation for SPG, Chediak-Higashi syndrome or other conditions characterized by an alteration in defensin concentration. Zamp1 polypeptides can be detected using immunoassay techniques and antibodies capable of recognizing a zamp1 polypeptide epitope. More specifically, the present invention contemplates methods for detecting zamp1 polypeptide comprising:

exposing a solution or sample or cell culture lysate or supernatant, possibly containing zamp1 polypeptide, to an antibody attached to a solid support, wherein said antibody binds to a first epitope of a zamp1 polypeptide;

washing said immobilized antibody-polypeptide to remove unbound contaminants;

exposing the immobilized antibody-polypeptide to a second antibody directed to a second epitope of a zamp1 polypeptide, wherein the second antibody is associated with a detectable label; and detecting the detectable label. Zamp1 polypeptide concentration differing from that of controls may be indicative of SPG, Chediak-Higashi syndrome or other conditions characterized by an alteration in defensin concentration. In addition, expression of zamp1 may be monitored in cystic fibrosis patients as a predictor of the onset of infectious crises. Also, high defensin, such as zamp1 polypeptide, levels have been associated with cytotoxic effects in lung, indicating that zamp1 polypeptide levels can be used to direct treatment for averting or addressing such cytotoxicity. For example, antibodies directed to zamp1 polypeptide can be administered to inactivate the same in a treatment modality.

Within additional aspects of the invention there are provided antibodies or synthesized binding proteins(e.g., those generated by phage display, *E. coli* Fab, and the like) that specifically bind to the zamp1 polypeptides described above. Such antibodies are useful for, among other uses as described herein, preparation of anti-idiotypic antibodies. Synthesized binding proteins may be produced by phage display using commercially available kits, such as the Ph.D.™ Phage Display Peptide Library Kits available from New England Biolabs, Inc. (Beverly, Mass.). Phage display techniques are described, for example, in U.S. Pat. Nos. 5,223,409, 5,403,484 and 5,571,698.

An additional aspect of the present invention provides methods for identifying agonists or antagonists of the zamp1 polypeptides disclosed above, which agonists or antagonists may have valuable properties as discussed further herein. Within one embodiment, there is provided a method of identifying zamp1 polypeptide agonists, comprising providing cells responsive thereto, culturing the cells in the presence of a test compound and comparing the cellular response with the cell cultured in the presence of the zamp1 polypeptide, and selecting the test compounds for which the cellular response is of the same type.

Within another embodiment, there is provided a method of identifying antagonists of zamp1 polypeptide, comprising providing cells responsive to a zamp1 polypeptide, culturing a first portion of the cells in the presence of zamp1 polypeptide, culturing a second portion of the cells in the presence of the zamp1 polypeptide and a test compound, and detecting a decrease in a cellular response of the second portion of the cells as compared to the first portion of the cells.

A further aspect of the invention provides a method of studying chemoattraction of monocytes in cell culture, comprising incubating monocytes in a culture medium comprising a zamp1 polypeptide, fragment, fusion protein, antibody, agonist or antagonist to study or evaluate monocyte chemoattraction. Such evaluation may be conducted using methods known in the art, such as those described by Territo et al. referenced above.

Melanocortin receptors are G-coupled protein receptors which activate adenylate cyclase and cause calcium flux. The agouti protein (which contains a 36 amino acid domain that is toxin-like) is thought to inhibit the binding of MSH-alpha to MC1 and MC4. In addition, the agouti protein is thought to be an antagonist of calcium channels, and certain toxins are believed to modulate ion flux. Experimental evidence has been generated, suggesting that defensins are capable of blocking calcium channels.

A further aspect of the invention provides a method of studying activity of the melanocortin family of receptors in cell culture, comprising incubating cells that endogenously bear such receptors (e.g., ACTH receptors or the like) or cells that have been engineered to bear such receptors in a culture medium comprising a ligand or putative ligand and zamp1 polypeptide, fragment, fusion protein, antibody, agonist or antagonist to study or evaluate ligand or putative ligand binding and/or ion flux regulation or modulation. Such evaluation may be conducted using methods known in the art, such as those described by Zhu et al. referenced above.

A further aspect of the invention provides a method of studying ion flux in cell culture, comprising incubating cells that are capable of ion flux, such as calcium flux, sodium flux, potassium flux or the like, in a culture medium comprising zamp1 polypeptide, fragment, fusion protein, antibody, agonist or antagonist to study or evaluate ion flux regulation or modulation.

A further aspect of the invention provides a method of studying cytocidal activity against mammalian cells, such as tumor cells, in cell culture, comprising incubating such cells in a culture medium comprising a zamp1 polypeptide, fragment, fusion protein, antibody, agonist or antagonist at high test agent and low cell concentration to study or evaluate cytocidal activity. Such evaluation may be conducted using methods known in the art, such as those described by Lichtenstein et al., *Blood* 68: 1407-10, 1986 and Sheu et al., *Antimicrob. Agents Chemother.* 28: 626-9, 1993.

Another aspect of the present invention involves the use of zamp1 polypeptides, fragments, fusion proteins or agonists as cell culture reagents in in vitro studies of exogenous microorganism infection, such as bacterial, viral or fungal infection. Such moieties may also be used in in vivo animal models of infection.

An additional aspect of the present invention is to study epithelial cell defensin induction in cell culture. In this aspect of the present invention, epithelial cells are cultured and exposed to pathogenic stimuli. Induction of zamp1 polypeptide production by the epithelial cells is then measured.

Within preferred embodiments of the invention the isolated polynucleotides will hybridize to similar sized regions of SEQ ID NO:2, SEQ ID NO:3, SEQ ID NO: 10, other probe sequences specifically set forth herein, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for isolating DNA and RNA are well known in the art. It is generally preferred to isolate RNA from bronchial epithelium, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-1412, 1972). Complementary DNA (cDNA) is prepared from poly(A)$^+$ RNA using known methods. Polynucleotides encoding zamp1 polypeptides are then identified and isolated by, for example, hybridization or PCR.

The present invention further provides counterpart polypeptides and polynucleotides from other species (orthologs). These species include, but are not limited to mammalian, avian, amphibian, reptile, fish, insect and other vertebrate and invertebrate species. Of particular interest are zamp1 polypeptides from other mammalian species, including murine, rat, porcine, ovine, bovine, canine, feline, equine and other primate proteins. Species homologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue of cell line. A zamp1 polypeptide-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to zamp1 polypeptide. Similar techniques can also be applied to the isolation of genomic clones.

Those skilled in the art will recognize that the sequences disclosed in SEQ ID NO:1, SEQ ID NO:2, SEQ ID NO:9 and SEQ ID NO:10 represent a single allele of the human zamp1 gene and polypeptide, and that allelic variation and alternative splicing are expected to occur. Allelic variants can be cloned by probing cDNA or genomic libraries from different individuals according to standard procedures. Allelic variants of the DNA sequence shown in SEQ ID NO:2 and SEQ ID NO:10, including those containing silent mutations and those in which mutations result in amino acid sequence changes, are within the scope of the present invention.

Within preferred embodiments of the invention, the isolated nucleic acid molecules can hybridize under stringent conditions to nucleic acid molecules having at least a portion of the nucleotide sequence of SEQ ID NOs:1, 4, 9 or 11 or to nucleic acid molecules having a nucleotide sequence complementary to those sequences. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5-25° C. below the $T_m$ of the hybrid and a hybridization buffer having up to 1 M Na$^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20-70° C. and a hybridization buffer containing up to 6×SSC and 0-50% formamide. A higher degree of stringency can be achieved at temperatures of from 40-70° C. with a hybridization buffer having up to 4×SSC and from 0-50% formamide. Highly stringent conditions typically encompass temperatures of 42-70° C. with a hybridization buffer having up to 1×SSC and 0-50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual,* Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques,* (Academic Press, Inc. 1987); and Wetmur, *Crit. Rev. Biochem. Mol. Biol.* 26:227 (1990)). Sequence analysis software, such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxyuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a Na$^+$ source, such as SSC (1×SSC: 0.15 M sodium chloride, 15 mM sodium citrate) or SSPE (1×SSPE: 1.8 M NaCl, 10 mM NaH2PO$_4$, 1 mM EDTA, pH 7.7). By decreasing the ionic concentration of the buffer, the stability of the hybrid is increased. Typically, hybridization buffers contain from between 10 mM-1 M Na$^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant zamp1 polypeptide can be hybridized with a nucleic acid molecule having at least a portion of the nucleotide sequence of SEQ ID NOs:1, 4, 9 or 11 (or their complements) at 42° C. overnight in a solution comprising 50% formamide, 5×SSC (1×SSC: 0.15 M sodium chloride and 15 mM sodium citrate), 50 mM sodium phosphate (pH 7.6), 5× Denhardt's solution (100× Denhardt's solution: 2% (w/v) FICOLL® 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher or lower temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant zamp1 polypeptide hybridize with a nucleic acid molecule having at least a portion of the nucleotide sequence of SEQ ID NOs:1, 4, 9 or 11 (or their complements) under stringent washing conditions, in which the wash stringency is equivalent to 0.5×-2×SSC with 0.1% SDS at 50-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. In other words, nucleic acid molecules encoding a variant zamp1 polypeptide hybridize with a nucleic acid molecule having at least a portion of the nucleotide sequence of SEQ ID NOs:1, 4, 9 or 11 (or their complements) under highly stringent washing conditions, in which the wash stringency is equivalent to 0.1×-0.2×SSC with 0.1% SDS at 50-65° C., including 0.1× SSC with 0.1% SDS at 50° C., or 0.2×SSC with 0.1% SDS at 65° C.

The present invention also contemplates zamp1 variant nucleic acid molecules that can be identified using two criteria: a determination of the similarity between the encoded polypeptide with the amino acid sequence of SEQ ID NOs:2 or 10, and a hybridization assay, as described above. Such zamp1 variants include nucleic acid molecules (1) that hybridize with at least a portion of a nucleic acid molecule having the nucleotide sequence of SEQ ID NO:1, 4, 9 or 11 (or their complements) under stringent washing conditions, in which the wash stringency is equivalent to 0.5×-2×SSC with 0.1% SDS at 50-65° C., and (2) that encode a polypeptide having at least 80%, at least 90%, at least 95% or greater than 95% sequence identity to the amino acid sequence of SEQ ID NOs:2 or 10. Alternatively, zamp1 variants can be characterized as nucleic acid molecules (1) that hybridize with a nucleic acid molecule having at least a portion of the nucleotide sequence of SEQ ID NO:1, 4, 9 or 11 (or their complements) under highly stringent washing conditions, in which the wash stringency is equivalent to 0.1×-0.2×SSC with 0.1% SDS at 50-65° C., and (2) that encode a polypeptide having at least 80%, at least 90%, at least 95% or greater than 95% sequence identity to the amino acid sequence of SEQ ID NOs:2 or 10.

The present invention also provides isolated zamp1 polypeptides that are substantially homologous to the polypeptides of SEQ ID NO:2 and SEQ ID NO:10 and their species homologs/orthologs. The term "substantially homologous" is used herein to denote polypeptides having 50%, preferably 60%, more preferably at least 80%, sequence identity to the sequences shown in SEQ ID NO:2 or SEQ ID NO:10 or their orthologs or paralogs. Such polypeptides will more preferably be at least 90% identical, and most preferably 95% or more identical to SEQ ID NO:2 or SEQ ID NO:10 or its orthologs or paralogs. Percent sequence identity is determined by conventional methods.

See, for example, Altschul et al., *Bull. Math. Bio.* 48: 603-616, 1986 and Henikoff and Henikoff, *Proc. Natl. Acad. Sci. USA* 89:10915-10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{(Total number of identical matches)}}{[\text{Length of the longer sequence plus the number of gaps introduced into the longer sequence in order to align the two sequences}]} \times 100$$

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zamp1. The FASTA algorithm is described by Pearson and Lipman, *Proc. Nat. Acad. Sci. USA* 85:2444, 1988, and by Pearson, *Meth. Enzymol.* 183:63, 1990.

Briefly, FASTA first characterizes sequence similarity by identifying regions shared by the query sequence (e.g., SEQ ID NOs:2 or 10) and a test sequence that have either the highest density of identities (if the ktup variable is 1) or pairs of identities (if ktup=2), without considering conservative amino acid substitutions, insertions, or deletions. The ten regions with the highest density of identities are then re-scored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63, 1990.

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The present invention includes nucleic acid molecules that encode a polypeptide having one or more "conservative amino acid substitutions," compared with the amino acid sequence of SEQ ID NOs:2 or 10. Conservative amino acid substitutions can be based upon the chemical properties of the amino acids. That is, variants can be obtained that contain one or more amino acid substitutions of SEQ ID NOs:2 or 10, in which an alkyl amino acid is substituted for an alkyl amino acid in a zamp1 amino acid sequence, an aromatic amino acid is substituted for an aromatic amino acid in a zamp1 amino acid sequence, a sulfur-containing amino acid is substituted for a sulfur-containing amino acid in a zamp1 amino acid sequence, a hydroxy-containing amino acid is substituted for a hydroxy-containing amino acid in a zamp1 amino acid sequence, an acidic amino acid is substituted for an acidic amino acid in a zamp1 amino acid sequence, a basic amino acid is substituted for a basic amino acid in a zamp1 amino acid sequence, or a dibasic monocarboxylic amino acid is substituted for a dibasic monocarboxylic amino acid in a zamp1 amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Table 4 also provided common conservative amino acid substitutions.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Natl. Acad. Sci. USA* 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in a zamp1 gene can be introduced by substituting nucleotides for the nucleotides recited in SEQ ID NOs:1 or 9. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). The ability of such variants to promote the anti-microbial or other properties of the wild-type protein can be determined using a standard methods, such as the assays described herein. Alternatively, a variant zamp1 polypeptide can be identified by the ability to specifically bind anti-zamp1 antibodies.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a polyhistidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459-463, 1982; Guan et al., *Gene* 67:21-30, 1987), thioredoxin, ubiquitin, cellulose binding protein, T7 polymerase, or other antigenic epitope or binding domain. See, in general Ford et al., *Protein Expression and Purification* 2: 95-107, 1991. DNAs encoding affinity tags are available from commercial suppliers (e.g., Pharmacia Biotech, Piscataway, N.J.; New England Biolabs, Beverly, Mass.). Polypeptides comprising affinity tags can further comprise a proteolytic cleavage site between the zamp1 polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise, in addition to the 20 standard amino acids, non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethyl-cysteine, hydroxyethylhomocysteine, nitroglutamine, homoglutamine, pipecolic acid, tert-leucine, norvaline, 2-azaphenylalanine, 3-azaphenylalanine, 4-azaphenyl-alanine, 4-fluorophenylalanine, 4-hydroxyproline, 6-N-methyl lysine, 2-aminoisobutyric acid, isovaline and α-methyl serine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations are carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Meth. Enzymol.* 202:301, 1991; Chung et al., *Science* 259:806-09, 1993; and Chung et al., *Proc. Natl. Acad. Sci. USA* 90:10145-49, 1993). In a second method, translation is carried out in Xenopus oocytes by microinjection of mutated mRNA and chemically aminoacylated suppressor tRNAs (Turcatti et al., *J. Biol. Chem.* 271:19991-98, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-76, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for zamp1 polypeptide amino acid residues.

"Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the zamp1 polypeptides of the present invention can be identified according to procedures known in the art, such as site-directed mutagenesis or alanine-scanning mutagenesis (Cunningham and Wells, *Science* 244: 1081-1085, 1989). In the latter technique, single alanine mutations are introduced at every residue in the molecule, and the resultant mutant molecules are tested for biological activity (e.g., anti-microbial activity) to identify amino acid residues that are critical to the activity of the molecule. See also, Hilton et al., *J. Biol. Chem.* 271:4699-4708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-312, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related β-defensins.

Multiple amino acid substitutions can be made and tested using known methods of mutagenesis and screening, such as those disclosed by Reidhaar-Olson and Sauer (*Science* 241: 53-57, 1988) or Bowie and Sauer (*Proc. Natl. Acad. Sci. USA* 86:2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zamp1 DNA and polypeptide sequences can be generated through DNA shuffling as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput, automated screening methods to detect activity of cloned, mutagenized polypeptides in host cells. Mutagenized DNA molecules that encode active polypeptides (e.g., anti-microbial activity) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 1 to 65 of SEQ ID NO: 2 or to residues 1 to 67 of SEQ ID NO: 10, residues 30 or 31 to residues 63 or 64 of SEQ ID NO:2 or polypeptides of SEQ ID NOs:14, 15 or 16, or allelic variants thereof and retain the anti-microbial properties of the wild-type protein. Such polypeptides may include additional amino acids from affinity tags and the like. Such polypeptides may also include additional polypeptide segments as generally disclosed above.

The polypeptides of the present invention, including full-length proteins, fragments thereof and fusion proteins, can be produced in genetically engineered host cells according to conventional techniques. However, host cells must be selected with some care as a result of the anti-microbial activity of the molecules of the present invention. For example, any cell culture-based system must be evaluated, because zamp1 polypeptides, fragments, fusion proteins, antibodies, agonists or antagonists may kill the host cell as a part of an anti-microbial function. Zamp1 polypeptides are of a small enough size to permit preparation by PCR or other protein chemistry techniques to avoid any potential host cell toxicity problems. Alternatively, native or engineered precursor proteins, prior to post-translational cleavage to yield the mature zamp1 polypeptide, are inactive, thereby limiting host cell cytotoxicity prior to lysosomal packaging. See, for example, Lehrer et al., *Cell* 64: 229-30, 1991. Thus, precursor proteins to zamp1 polypeptides may be produced in microbial cell culture.

Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al. (eds.), *Current Protocols in Molecular Biology*, John Wiley and Sons, Inc., NY, 1987.

In general, a DNA sequence encoding a zamp1 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zamp1 polypeptide into the secretory pathway of a host cell, a secretory signal sequence (also known as a leader sequence, prepro sequence or pre sequence) is provided in the expression vector. The secretory signal sequence may be that of the zamp1 polypeptide, or may be derived from another secreted protein (e.g., t-PA) or synthesized de novo. The secretory signal sequence is joined to the zamp1 polypeptide-encoding DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residues 1-18 or 12 of SEQ ID NO:2 or amino acid residues 1-20 or 22 of SEQ ID NO:10, is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), DEAE-dextran mediated transfection (Ausubel et al., eds., *Current Protocols in Molecular Biology*, John Wiley and Sons, Inc., NY, 1987), liposome-mediated transfection (Hawley-Nelson et al., *Focus* 15:73, 1993; Ciccarone et al., *Focus* 15:80, 1993), and viral vectors (A. Miller and G. Rosman, *BioTechniques* 7:980-90, 1989; Q. Wang and M. Finer, *Nature Med.* 2:714-16, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Preferred cultured mammalian cells include the COS-1 (ATCC No. CRL 1650), COS-7 (ATCC No. CRL 1651), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding the zamp1 polypeptide is inserted into the baculoviral genome in place of the AcNPV polyhedrin gene coding sequence by one of two methods. The first is the traditional method of homologous DNA recombination between wild-type AcNPV and a transfer vector containing the zamp1 flanked by ACNPV sequences. Suitable insect cells, e.g. SF9 cells, are infected with wild-type AcNPV and transfected with a transfer vector comprising a zamp1 polynucleotide operably linked to an AcNPV polyhedrin gene promoter, terminator, and flanking sequences. See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and, Richardson, C. D., Ed., *Baculovirus Expression Protocols, Methods in Molecular Biology*, Totowa, N.J., Humana Press, 1995. Natural recombination within an insect cell will result in a recombinant baculovirus which contains zamp1 driven by the polyhedrin promoter. Recombinant viral stocks are made by methods commonly used in the art.

The second method of making recombinant baculovirus utilizes a transposon-based system described by Luckow (Luckow et al., *J Virol.* 67:4566-79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zamp1 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zamp1. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkin and Possee, *J. Gen. Virol.* 71:971-6, 1990; Bonning. et al., *J. Gen. Virol.* 75:1551-6, 1994; and, Chazenbalk and Rapoport, *J. Biol. Chem.* 270: 1543-9, 1995. In such transfer vector constructs, a short or long version of the basic protein promoter can be used. Moreover, transfer vectors can be constructed which replace the native zamp1 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zamp1 secretory signal sequence. In addition, transfer vectors can include an in-frame fusion with DNA encoding an epitope tag at the C- or N-terminus of the expressed zamp1 polypeptide, for example, a Glu-Glu epitope tag (Grussenmeyer et al., *Proc. Natl. Acad. Sci.* 82:7952-4, 1985). Using a technique known in the art, a transfer vector containing zamp1 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zamp1 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. The recombinant virus-infected cells typically produce the recombinant zamp1 polypeptide at 12-72 hours post-infection and secrete it with varying efficiency into the medium. The culture is usually harvested 48 hours post-infection. Centrifugation is used to separate the cells from the medium (supernatant). The supernatant containing the zamp1 polypeptide is filtered through micropore filters, usually 0.45 µm pore size. Procedures used are generally described in available laboratory manuals (King and Possee, ibid.; O'Reilly et al., ibid.; Richardson, ibid.). Subsequent purification of the zamp1 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459-65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zamp1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Expressed recombinant zampi polypeptides (or chimeric zampi polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow SEPHAROSE® (Pharmacia, Piscataway, N.J.) being particularly preferred. Exemplary chromatographic media include those media derivatized with phenyl, butyl, or octyl groups, such as PhenylSEPHAROSE® (Pharmacia), TOYOPEARL® butyl 650 (Toso Haas, Montgomeryville, Pa.), Octyl-SEPHAROSE® (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their structural properties. For example, immobilized metal ion adsorption (IMAC) chromatography can be used to purify histidine-rich proteins or proteins having a His-affinity tag. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529-39). Within additional embodiments of the invention, a fusion of the polypeptide of interest and an affinity tag (e.g., maltose-binding protein, an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zamp1 polypeptides or fragments thereof may also be prepared through chemical synthesis. Zamp1 polypeptides may be monomers or multimers; glycosylated or non-glycosylated; pegylated or non-pegylated; amidated or non-amidated; sulfated or non-sulfated; and may or may not include an initial methionine amino acid residue. For example, zamp1 polypeptides can be synthesized by exclusive solid phase synthesis, partial solid phase methods, fragment condensation or classical solution synthesis. The polypeptides are preferably prepared by solid phase peptide synthesis, for example as described by Merrifield, *J. Am. Chem. Soc.* 85:2149, 1963. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxycarbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc.

The side-chain protecting groups selected must remain intact during coupling and not be removed during the deprotection of the amino-terminus protecting group or during coupling conditions. The side-chain protecting groups must also be removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for arginine, cyclohexyl for aspartic acid, 4-methylbenzyl (and acetamidomethyl) for cysteine, benzyl for glutamic acid, serine and threonine, benzyloxymethyl (and dinitrophenyl) for histidine, 2-Cl-benzyloxycarbonyl for lysine, formyl for tryptophan and 2-bromobenzyl for tyrosine. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for arginine, trityl for asparagine, cysteine, glutamine and histidine, tert-butyl for aspartic acid, glutamic acid, serine, threonine and tyrosine, tBoc for lysine and tryptophan.

For the synthesis of phosphopeptides, either direct or post-assembly incorporation of the phosphate group is used. In the direct incorporation strategy, the phosphate group on serine, threonine or tyrosine may be protected by methyl, benzyl, or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl groups of serine, threonine or tyrosine are derivatized on solid phase with di-tert-butyl-, dibenzyl- or dimethyl-N,N'-diisopropyl-phosphoramidite and then oxidized by tert-butylhydro-peroxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlorotrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) are used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al., "Solid Phase Peptide Synthesis" (2nd Edition), (Pierce Chemical Co., Rockford, Ill., 1984) and Bayer and Rapp, *Chem. Pept. Prot.* 3:3, 1986; and Atherton et al., Solid Phase Peptide Synthesis: *A Practical Approach*, IRL Press, Oxford, 1989.

The C-terminal amino acid, protected at the side chain if necessary, and at the alpha-amino group, is attached to a hydroxylmethyl resin using various activating agents including dicyclohexylcarbodiimide (DCC), N,N'-diisopropylcarbodiimide (DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300-320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluorophosphate (BOP) and its pyrrolidine analog (PyBOP), bromo-tris-pyrrolidino-phosphonium hexafluorophosphate (PyBrOP), O-(benzotriazol-1-yl)-1,1,3,3-tetramethyl-uronium hexafluorophosphate (HBTU) and its tetrafluoroborate analog (TBTU) or its pyrrolidine analog (HBPyU), O-(7-azabenzotriazol-1-yl)-1,1,3,3-tetramethyl-uronium hexafluorophosphate (HATU) and its tetrafluoroborate analog (TATU) or its pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, CH2Cl2 or mixtures thereof. The extent of completion of the coupling reaction can be monitored at each stage, e.g., by the ninhydrin reaction as described by Kaiser et al., *Anal. Biochem.* 34:595, 1970.

After the entire assembly of the desired peptide, the peptide-resin is cleaved with a reagent with proper scavengers. The Fmoc peptides are usually cleaved and deprotected by TFA with scavengers (e.g., H2O, ethanedithiol, phenol and thioanisole). The tBoc peptides are usually cleaved and deprotected with liquid HF for 1-2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of tryptophan and the dinitrophenyl group of histidine need to be removed, respectively by piperidine and thiophenyl in DMF prior to the HF cleavage. The acetamidomethyl group of cysteine can be removed by mercury(II)acetate and alternatively by iodine, thallium(III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

A zamp1 polypeptide ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253: 545-48, 1991; Cunningham et al., *Science* 245:821-25, 1991).

Zamp1 polypeptides can also be used to prepare antibodies that specifically bind to zamp1 polypeptide epitopes, peptides or polypeptides. Methods for preparing polyclonal and monoclonal antibodies are well known in the art (see, for example, Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982). As would be evident to one of ordinary skill in the art, polyclonal antibodies can be generated from a variety of warm-blooded animals, such as horses, cows, goats, sheep, dogs, chickens, rabbits, mice, and rats.

The immunogenicity of a zamp1 polypeptide may be increased through the use of an adjuvant, such as alum (aluminum hydroxide) or Freund's complete or incomplete adjuvant. Polypeptides useful for immunization also include fusion polypeptides, such as fusions of zamp1 polypeptide or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included; Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to zamp1 protein or peptide, and selection of antibody display libraries in phage or similar vectors (for instance, through use of immobilized or labeled zamp1 protein or peptide).

Antibodies are defined to be specifically binding if: 1) they exhibit a threshold level of binding activity, and/or 2) they do not significantly cross-react with related polypeptide molecules. First, antibodies herein specifically bind if they bind to a zamp1 polypeptide, peptide or epitope with a binding affinity (Ka) of $10^6$ mol$^{-1}$ or greater, preferably $10^7$ mol$^{-1}$ or greater, more preferably $10^8$ mol$^{-1}$ or greater, and most preferably $10^9$ mol$^{-1}$ or greater. The binding affinity of an antibody can be readily determined by one of ordinary skill in the art, for example, by Scatchard analysis (G. Scatchard, *Ann. NY Acad. Sci.* 51: 660-72, 1949).

Second, antibodies specifically bind if they do not significantly cross-react with related polypeptides. Antibodies do not significantly cross-react with related polypeptide molecules, for example, if they detect human zamp1 polypeptide, but not known related polypeptides using a standard Western blot analysis (Ausubel et al., ibid.). Examples of known related polypeptides are orthologs, that is, proteins from the same species that are members of a protein family, such as other known human β-defensins (e.g., hBD-1 and hBD-2), mutant human β-defensins, and non-human β-defensins.

Moreover, antibodies may be "screened against" known related polypeptides to isolate a population that specifically binds to the inventive polypeptides. For example, antibodies raised to human zamp1 polypeptide are adsorbed with related polypeptides adhered to an insoluble matrix; antibodies specific to human zamp1 polypeptide will flow through the matrix under the proper buffer conditions. Such screening allows isolation of polyclonal and monoclonal antibodies non-crossreactive to closely related polypeptides (see, Antibodies: A Laboratory Manual, Harlow and Lane (eds.), Cold Spring Harbor Laboratory Press, 1988; Current Protocols in Immunology, Cooligan et al. (eds.), National Institutes of Health, John Wiley and Sons, Inc., 1995). Screening and isolation of specific antibodies is well known in the art (see, Fundamental Immunology, Paul (ed.), Raven Press, 1993; Getzoff et al., *Adv. Immunol.* 43:1-98, 1988; Monoclonal Antibodies: Principles and Practice, Goding, J. W. (eds.), Academic Press Ltd., 1996; Benjamin et. al., *Ann. Rev. Immunol.* 2:67-101, 1984).

A variety of assays known to those skilled in the art can be utilized to detect antibodies which specifically bind to zamp1 proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zamp1 protein or peptide.

Antibodies to zamp1 polypeptides may be used for tagging cells that express zamp1 polypeptides; for isolating zamp1 polypeptides by affinity purification; for diagnostic assays for determining circulating levels of zamp1 polypeptides; for detecting or quantitating soluble zamp1 polypeptide as a marker of underlying pathology or disease; in analytical methods employing FACS; for screening expression libraries; for generating anti-idiotypic antibodies; and as neutralizing antibodies or as antagonists to block antimicrobial activity in vitro and in vivo.

For pharmaceutical use, the proteins of the present invention are formulated for topical, inhalant or parenteral, particularly intravenous or subcutaneous, delivery according to conventional methods. Intravenous administration will be by bolus injection or infusion over a typical period of one to several hours. In general, pharmaceutical formulations will include a zamp1 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

The invention is further illustrated by the following non-limiting examples.

EXAMPLE 1

Extension of EST Sequence

The novel zamp1 polypeptides of the present invention were initially identified by querying an EST database for homologous sequences to the SAP-1 human defensin isolated from human psoriatic skin. A single EST sequence was discovered in a bronchial epithelium cDNA library and was predicted to be related to the β-defensin family. A second search based upon the β-defensin consensus motif also identified the EST.

To identify the corresponding cDNA, a clone containing the EST was sought, but was not located. Oligonucleotides ZC14741 (SEQ ID NO: 5), ZC14740 (SEQ ID NO: 6) were used in a PCR reaction to isolate the zamp1 polypeptide-encoding sequence from human genomic DNA. Reaction conditions were 94° C. for 1 minute and 30 seconds, followed by 35 cycles of 94° C. for 10 seconds, 58° C. for 20 seconds and 72° C. for 20 seconds, followed by 72° C. for ten minutes. As a template, 100 ng of human genomic DNA was used, and Clontech Advantage PCR mix (Clontech, Palo Alto, Calif.) was used as the polymerase mixture. The resulting 113 bp fragment was then purified on a 3.2% NuSieve (FMC Bioproducts, Rockland, Me.) gel using a QiaexII Gel Extraction Kit (Qiagen, Inc., Chatsworth, Calif.) according to the manufacturer's directions. The purified material was used as a template for sequencing. The template was sequenced on an ABIPRISM™ model 377 DNA sequencer (Perkin-Elmer Cetus, Norwalk, Conn.) using the ABI PRISM™ Dye Terminator Cycle Sequencing Ready Reaction Kit (Perkin-Elmer Corp.) according to manufacturer's instructions. Oligonucleotides ZC14741 (SEQ ID NO: 5), ZC14740 (SEQ ID NO: 6) were used as primers for sequencing the clone. Sequencing reactions were carried out in a Hybaid OmniGene Temperature Cycling System (National Labnet Co., Woodbridge, N.Y.). SEQUENCHER™ 3.1 sequence analysis software (Gene Codes Corporation, Ann Arbor, Mich.) was used for data analysis. The resulting 113 bp sequence is disclosed in SEQ ID NO: 1. Comparison of the originally derived EST sequence with the sequence represented in SEQ ID NO: 1 showed that there were 2 base pair differences which resulted in 1 amino acid difference between the deduced amino acid sequences. Note that one of the base pair differences were from unknown "N" residues in the EST sequence to known residues in SEQ ID NO: 1.

Generally, one or a combination of several techniques could be used to obtain the full length sequence of the zamp1 polypeptide-encoding polynucleotide. First, if one or more additional ESTs are identified that contig to the clone sequenced above, clones corresponding to such ESTs can be ordered and sequenced as described above and spliced together with the original sequence to form the full length sequence. If a small portion of the full length sequence is absent, 5' RACE reactions can be done, and the resulting fragments can be sequenced as described above and spliced together with the original sequence to form the full length sequence. Also, one or more cDNA libraries can be probed with all or a portion of SEQ ID NO: 1 to identify a putative full-length clone. Such a full length clone can be sequenced as described above.

EXAMPLE 2

Tissue Distribution

Northerns were performed using Human Multiple Tissue Blots from Clontech (Palo Alto, Calif.). An approximately 113 bp DNA probe, based directly on the identified EST, was generated using PCR techniques, specifically a 35 cycle reaction with an annealing temperature of 58° C. using Clontech Advantage KlenTaq Polymerase mix (Clontech). The DNA probe was radioactively labeled with $^{32}P$ using REDIPRIME™ DNA labeling system (Amersham, Arlington Heights, Ill.) according to the manufacturers specifications. The probe was purified using a NUCTRAP push column (Stratagene Cloning Systems, La Jolla, Calif.). EXPRESSHYB (Clontech) solution was used for prehybridization and as a hybridizing solution for the Northern blots. Hybridization took place overnight at 55° C., and the blots were then washed in 2×SSC and 0.1% SDS at RT, followed by a wash in 0.1×SSC and 0.10% SDS at 50° C. No expression was observed. It thus appears that normal tissue levels of mRNA of zamp1 polypeptide are below the detection sensitivity of the Northern blot. Such an observation is consistent with the knowledge in the art regarding some defensins, i.e., that they are constitutively expressed at low levels but are highly inducible upon infection.

EXAMPLE 3

Chromosomal Mapping of the Zamp1 Gene

The zamp1 gene was mapped to chromosome 8 using the commercially available "GeneBridge 4 Radiation Hybrid Panel" (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server located on the Internet allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of the zamp1 gene with the "GeneBridge 4 RH Panel", 20 µl reactions were set up in a PCRable 96-well microtiter plate (Stratagene, La Jolla, Calif.) and used in a "RoboCycler Gradient 96" thermal cycler (Stratagene). Each of the 95 PCR reactions consisted of 2 µl 10×KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC 14,780 (SEQ ID NO: 7), 1 µl antisense primer, ZC 14,776 (SEQ ID NO: 8), 2 µl "RediLoad" (Research Genetics, Inc., Huntsville, Ala.), 0.4 µl 50×Advantage KlenTaq Polymerase Mix (Clontech Laboratories, Inc.), 25 ng of DNA from an individual hybrid clone or control and x µl ddH2O for a total volume of 20 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 52° C. and 1.5 minute extension at 72° C., followed by a final 1 cycle extension of 7 minutes at 72° C. The reactions were separated by electrophoresis on a 2% agarose gel (Life Technologies, Gaithersburg, Md.).

The results showed that the zampi gene maps 33.5 cR_3000 from the top of the human chromosome 8 linkage group on the WICGR radiation hybrid map. Proximal and distal framework markers were CHLC.GATA62D10 and WI-3823 (D8S1511), respectively. The use of surrounding markers positions the zampi gene in the 8p23.3-p23.2 region on the integrated LDB chromosome 8 map (The Genetic Location Database, University of Southhampton, WWW server located on the Internet).

EXAMPLE 4

Identification of DNA Encoding full Length Zamp1 Polypeptide and Sequencing thereof The 5' end of zamp1 coding sequence was obtained by PCR using GenomeWalker® reagents (Clontech) in combination with a zamp1 polypeptide-specific antisense primer ZC15591 (SEQ ID NO: 12) and then conducting nested PCR with ZC15589 (SEQ ID NO: 13), according to manufacturer's instructions, with the exception that 64° C. was used in the primary reaction instead of the suggested 67° C. PCR products were run on a 2% agarose gel (Gibco), and gel purified using Qiaex II reagents (Qiagen) according to manufacturer's instructions. Products were sequenced using ZC15589 (SEQ ID NO: 13) as a sequencing primer, revealing the extension of zamp1 polypeptide-encoding to a putative initiation methionine (nucleotides 1-201 or 1-219 of SEQ ID NO:9) and about 250 base pairs of 5' untranslated sequence.

EXAMPLE 5

Synthesis of Zamp1

A 45 amino acid residue zampi peptide (residues 23 to 67 of SEQ ID NO:10) was synthesized by solid phase peptide synthesis using a model 431A Peptide Synthesizer (Applied Biosystems/Perkin Elmer; Foster City, Calif.). Fmoc-Lysine (Boc) resin (0.52 mmol/g; Anaspec Inc., San Jose, Calif.) was used as the initial support resin. 1 mmol Amino acid cartridges (Anaspec Inc., San Jose, Calif. and Applied Biosystems/Perkin Elmer, Foster City, Calif.) were used for synthesis. 2-(1-H-benzotriazol-1-yl)-1,1,3,3-tetramethyuroniumhexafluorophosphate (HBTU), 1-Hydroxy-benzotriazole (HOBt), 2 M N,N-Diisopropylethylamine, N-Methylpyrrolidone, Dichloromethane (all from Applied Biosystems/Perkin Elmer, Foster City, Calif.), along with piperidine (Aldrich Chemical Co., St. Louis, Mo.) and 0.5 M acetic anhydride capping solution (Advanced ChemTech, Louisville, Ky.), were used as synthesis reagents.

The Peptide Companion software (Peptides International, Louisville, Ky.) was used to help predict the aggregation potential for the synthesis for zamp1. Synthesis was performed using both single and double coupling cycles. Also, acetylation was used where difficult couplings were predicted.

The peptide was cleaved from the solid phase by the standard TFA cleavage procedure (according to Peptide Cleavage manual, Applied Biosystems/Perkin Elmer). Purification of the peptide was done by RP-HPLC using a C18, 52 mm×250 mm, preparative column (Vydac, Hesperia, Calif.). Fractions from the column were collected and analyzed for the correct mass by electrospray mass spectrometry; the purity was analyzed by analytical RP-HPLC, using a C18, 4.6 mm×250 mm column (Vydac, Hesperia, Calif.). The mass spectrometry analysis confirmed the desired molecular weight of the reduced form of zamp1, i.e., 5158. Purified fractions were frozen and then lyophilized.

The reduced peptide was dissolved in 6 M guanidine HCl (Aldrich Chemical Co.) at an initial concentration of 2 mg/ml. This solution was then added slowly to 2.1 volume equivalents of 1 M guanidine HCl along with 0.52 volume equivalents of DMSO (Aldrich Chemical Co.). The oxidation was monitored with analytical RP-HPLC using the same analytical C18 column; the oxidation was complete at 48 hours. Salts were removed from the reaction mixture using solid phase extraction C18 cartridges (Waters, Milford, Mass.). The eluant containing the oxidized peptide is concentrated and then purified using RP-HPLC semi-prep C18 column (Vydac, Hesperia, Calif.). Four distinct peaks were determined to correspond to the fully oxidized form of zamp1 by electrospray LCMS. The peak referred to as peak 2, as it was the second peak to elude by RP-HPLC, was found to contain the conserved defensin disulfide pattern, by a process of elimination using partial digest and peptide mapping of all four peaks. This peak was isolated, frozen and lyophilized.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated protein comprising a polypeptide that is at least 95% identical to amino acid residues 21 to 65 of SEQ ID NO:2; wherein the polypeptide has antimicrobial activity.

2. The isolated protein of claim 1 wherein the amino acid percent identity is determined using a FASTA program with ktup=1, gap opening penalty=10, gap extension penalty=1, and substitution matrix=BLOSUM62, with other parameters set as default.

3. The isolated protein of claim 1 wherein the polypeptide comprises amino acid residues 21 to 65 of SEQ ID NO:2.

4. An isolated polypeptide comprising an amino acid sequence selected from the group consisting of:
   a) amino acid residue 30 to amino acid residue 63 of SEQ ID NO:2;
   b) amino acid residue 31 to amino acid residue 63 of SEQ ID NO:2;
   c) amino acid residue 30 to amino acid residue 64 of SEQ II) NO:2;
   d) amino acid residue 31 to amino acid residue 64 of SEQ ID NO:2; and
   e) amino acid residue 21 to amino acid residue 65 of SEQ ID NO:2, wherein the polypeptide has antimicrobial activity.

5. A pharmaceutical composition comprising a polypeptide comprising an amino acid sequence selected from the group consisting of:
   a) amino acid residue 1 to amino acid residue 65 of SEQ ID NO:2;
   b) amino acid residue 30 to amino acid residue 63 of SEQ ID NO:2;
   c) amino acid residue 31 to amino acid residue 63 of SEQ ID NO:2;
   d) amino acid residue 30 to amino acid residue 64 of SEQ ID NO:2;
   e) amino acid residue 31 to amino acid residue 64 of SEQ ID NO:2; and
   f) amino acid residue 21 to amino acid residue 65 of SEQ ID NO:2;
   in combination with a pharmaceutically acceptable vehicle, wherein the polypeptide has antimicrobial activity.

6. A pharmaceutical composition comprising a polypeptide that is at least 95% identical to amino acid residues 21 to 65 of SEQ ID NO:2 and a pharmaceutically acceptable carrier, wherein the polypeptide has antimicrobial activity.

7. A method of treating a microbial-related disease in a mammal comprising administering to the mammal a therapeutically effective amount of a polypeptide comprising an amino acid seciuence selected from the group consisting of:
   a) amino acid residue 1 to amino acid residue 65 of SEQ ID NO:2;
   b) amino acid residue 30 to amino acid residue 63 of SEQ ID NO:2;
   c) amino acid residue 31 to amino acid residue 63 of SEQ ID NO:2;
   d) amino acid residue 30 to amino acid residue 64 of SEQ ID NO:2; and
   e) amino acid residue 31 to amino acid residue 64 of SEQ ID NO:2;
   wherein said polypepiide ameliorates said disease.

8. The method of claim 7 wherein said microbial-related disease is associated with the eye.

9. The method of claim 8 wherein said microbial-related disease is conjunctivitis.

10. The method of claim 7 wherein said microbial-related disease is associated with the ear.

* * * * *

SEQUENCE LISTING

<160> NUMBER OF SEQ ID NOS: 72

<210> SEQ ID NO 1
<211> LENGTH: 219
<212> TYPE: DNA
<213> ORGANISM: Homo sapiens
<220> FEATURE:
<221> NAME/KEY: CDS
<222> LOCATION: (1)...(195)

<400> SEQUENCE: 1

```
atg agg atc cat tat ctt ctg ttt gct ttg ctc ttc ctg ttt ttg gtg      48
Met Arg Ile His Tyr Leu Leu Phe Ala Leu Leu Phe Leu Phe Leu Val
 1               5                  10                  15 cct gtt cca ggt cat gga gga atc ata aac aca tta cag aaa tat tat      96
Pro Val Pro Gly His Gly Gly Ile Ile Asn Thr Leu Gln Lys Tyr Tyr
            20                  25                  30 tgc aga gtc aga ggc ggc cgg tgt gct gtg ctc agc tgc ctt cca aag     144
Cys Arg Val Arg Gly Gly Arg Cys Ala Val Leu Ser Cys Leu Pro Lys
        35                  40                  45 gag gaa cag atc ggc aag tgc tcg acg cgt ggc cga aaa tgc tgc cga     192
Glu Glu Gln Ile Gly Lys Cys Ser Thr Arg Gly Arg Lys Cys Cys Arg
    50                  55                  60 aga aagaataaa aaccctgaaa catg                                       219
Arg
 65
```

<210> SEQ ID NO 2
<211> LENGTH: 65
<212> TYPE: PRT
<213> ORGANISM: Homo sapiens

<400> SEQUENCE: 2

```
Met Arg Ile His Tyr Leu Leu Phe Ala Leu Leu Phe Leu Phe Leu Val
 1               5                  10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg
65
```

<210> SEQ ID NO 3
<211> LENGTH: 31
<212> TYPE: PRT
<213> ORGANISM: Artificial Sequence
<220> FEATURE:
<221> NAME/KEY: VARIANT
<222> LOCATION: (2)...(7)
<223> OTHER INFORMATION: Any amino acid, preferably not cysteine.
<220> FEATURE:
<221> NAME/KEY: VARIANT
<222> LOCATION: (9)...(12)
<223> OTHER INFORMATION: Any amino acid, preferably not cysteine.
<220> FEATURE:
<221> NAME/KEY: VARIANT
<222> LOCATION: (14)...(20)
<223> OTHER INFORMATION: Any amino acid, preferably not cysteine.
<220> FEATURE:
<221> NAME/KEY: VARIANT
<222> LOCATION: (22)...(22)
<223> OTHER INFORMATION: Any amino acid, preferably not cysteine.

```
<221> NAME/KEY: VARIANT
<222> LOCATION: (24)...(29)
<223> OTHER INFORMATION: Any amino acid, preferably not cysteine.
<220> FEATURE:
<223> OTHER INFORMATION: conserved motif

<400> SEQUENCE: 3

Cys Xaa Xaa Xaa Xaa Xaa Xaa Cys Xaa Xaa Xaa Xaa Cys Xaa Xaa Xaa
 1               5                  10                  15

Xaa Xaa Xaa Xaa Gly Xaa Cys Xaa Xaa Xaa Xaa Xaa Xaa Cys Cys
            20                  25                  30

<210> SEQ ID NO 4
<211> LENGTH: 213
<212> TYPE: DNA
<213> ORGANISM: Artificial Sequence
<220> FEATURE:
<223> OTHER INFORMATION: Degenerate nucleotide encoding the polypeptide
      of SEQ ID NO:2.
<220> FEATURE:
<221> NAME/KEY: misc_feature
<222> LOCATION: (1)...(213)
<223> OTHER INFORMATION: n = a, g, c or t

<400> SEQUENCE: 4
athcaytayy  tnytnttygc  nytnytntty  ytnttyytng  tnccngtncc  nggncayggn     60
ggnathatha  ayacnytnca  raartrrnnn  tgymgngtnm  gnggnggnmg  ntgygcngtn    120
ytnwsntgyy  tnccnaarga  rgarcarath  ggnaartgyw  snacnmgngg  nmgnaartgy    180
tgymgnmgna  araartrraa  rccntrraay  atg                                  213

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide ZC14741

<400> SEQUENCE: 5
gagcacttgc  cgatctgttc                                                    20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide ZC14740

<400> SEQUENCE: 6
ccaggtcatg  gaggaatcat                                                    20

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide ZC14780

<400> SEQUENCE: 7
ggaggaatca  taaacaca                                                      18

<210> SEQ ID NO 8
<211> LENGTH: 18
<212> TYPE: DNA
<213> ORGANISM: Artificial Sequence
<220> FEATURE:
```

<223> OTHER INFORMATION: Oligonucleotide ZC14776

<400> SEQUENCE: 8
gccgatctgt tcctccttt                                                        18

<210> SEQ ID NO 9
<211> LENGTH: 438
<212> TYPE: DNA
<213> ORGANISM: Homo sapiens
<220> FEATURE:
<221> NAME/KEY: CDS
<222> LOCATION: (220)...(420)

<400> SEQUENCE: 9

```
acaaatccat agggagctct gccttaccat tgggttccta attaactgag tgagtgggtg      60
tgttctgcat ggtgagaggc attggaatga tgcatcagaa acatgtcat  aatgtcatca     120 ctgtaatatg acaagaattg cagctgtggc tggaaccttt ataaagtgac caagcacacc     180
ttttcatcca gtctcagcgt ggggtgaagc ctagcagct atg agg atc cat tat         234
                                            Met Arg Ile His Tyr
                                            1               5 ctt ctg ttt gct ttg ctc ttc ctg ttt ttg gtg cct gtt cca ggt cat        282
Leu Leu Phe Ala Leu Leu Phe Leu Phe Leu Val Pro Val Pro Gly His
            10                  15                  20 gga gga atc ata aac aca tta cag aaa tat tat tgc aga gtc aga ggc        330
Gly Gly Ile Ile Asn Thr Leu Gln Lys Tyr Tyr Cys Arg Val Arg Gly
        25                  30                  35 ggc cgg tgt gct gtg ctc agc tgc ctt cca aag gag gaa cag atc ggc        378
Gly Arg Cys Ala Val Leu Ser Cys Leu Pro Lys Glu Glu Gln Ile Gly
    40                  45                  50 aag tgc tcg acg cgt ggc cga aaa tgc tgc cga aga aag aaa                420
Lys Cys Ser Thr Arg Gly Arg Lys Cys Cys Arg Arg Lys Lys
55                  60                  65 taaaaaccct gaaacatg                                                    438
```

<210> SEQ ID NO 10
<211> LENGTH: 67
<212> TYPE: PRT
<213> ORGANISM: Homo sapiens

<400> SEQUENCE: 10

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 11
<211> LENGTH: 219
<212> TYPE: DNA
<213> ORGANISM: Artificial Sequence
<220> FEATURE:
<223> OTHER INFORMATION: Degenerate nucleotide sequence encoding the
      polypeptide of SEQ ID NO:10.
<220> FEATURE:
<221> NAME/KEY: misc_feature
<222> LOCATION: (1)...(219)

<223> OTHER INFORMATION: n = a, g, c or t

<400> SEQUENCE: 11

```
atgmgnathc aytayytnyt nttygcnytn ytnttyytnt tyytngtncc ngtnccnggn    60
cayggnggna thathaayac nytncaraar trrnnntgym gngtnmgngg nggnmgntgy   120
gcngtnytnw sntgyytncc naargargar carathggna artgywsnac nmgnggnmgn   180
aartgytgym gnmgnaaraa rtrraarccn trraaytg                          219
```

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide ZC15591

<400> SEQUENCE: 12

```
tgccgatctg ttcctccttt g                                             21
```

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide ZC15589

<400> SEQUENCE: 13

```
gaacaggcac caaaaacagg aagag                                         25
```

<210> SEQ ID NO 14
<211> LENGTH: 37
<212> TYPE: PRT
<213> ORGANISM: Artificial Sequence
<220> FEATURE:
<223> OTHER INFORMATION: Defensin polypeptide

<400> SEQUENCE: 14

```
Gln Lys Tyr Tyr Cys Arg Val Arg Tyr Tyr Arg Cys Ala Val Leu Ser
 1               5                  10                  15
Cys Leu Pro Lys Glu Glu Gln Ile Tyr Lys Cys Ser Thr Arg Tyr Arg
            20                  25                  30
Lys Cys Cys Arg Arg
        35
```

<210> SEQ ID NO 15
<211> LENGTH: 29
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (26)...(26)
<223> OTHER INFORMATION: leucine, isoleucine, valine, phenylalanine, or
      methionine

<400> SEQUENCE: 15

```
Gly Arg Cys Ala Val Leu Ser Cys Leu Pro Lys Glu Glu Cys Ile Gly
 1               5                  10                  15
Lys Met Ser Thr Arg Gly Arg Lys Cys Xaa Arg Arg Lys
            20                  25
```

<210> SEQ ID NO 16
<211> LENGTH: 30

```
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (26)...(26)
<223> OTHER INFORMATION: leucine, isoleucine, valine, phenylalanine, or
      methionine

<400> SEQUENCE: 16

Gly Arg Cys Ala Val Leu Ser Cys Leu Pro Lys Glu Glu Cys Ile Gly
 1               5                  10                  15

Lys Met Ser Thr Arg Gly Arg Lys Cys Xaa Arg Arg Lys Lys
             20                  25                  30

<210> SEQ ID NO 17
<211> LENGTH: 27
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (26)...(26)
<223> OTHER INFORMATION: leucine, isoleucine, valine, phenylalanine, or
      methionine

<400> SEQUENCE: 17

Gly Arg Cys Ala Val Leu Ser Cys Leu Pro Lys Glu Glu Cys Ile Gly
 1               5                  10                  15

Lys Met Ser Thr Arg Gly Arg Lys Cys Xaa Arg
             20                  25

<210> SEQ ID NO 18
<211> LENGTH: 38
<212> TYPE: PRT
<213> ORGANISM: Artificial Sequence
<220> FEATURE:
<223> OTHER INFORMATION: Defensin polypeptide

<400> SEQUENCE: 18

Gln Lys Tyr Tyr Cys Arg Val Arg Tyr Tyr Arg Cys Ala Val Leu Ser
 1               5                  10                  15

Cys Leu Pro Lys Glu Glu Gln Ile Tyr Lys Cys Ser Thr Arg Tyr Arg
             20                  25                  30

Lys Cys Cys Arg Arg Lys
         35

<210> SEQ ID NO 19
<211> LENGTH: 39
<212> TYPE: PRT
<213> ORGANISM: Artificial Sequence
<220> FEATURE:
<223> OTHER INFORMATION: Defensin polypeptide

<400> SEQUENCE: 19

Gln Lys Tyr Tyr Cys Arg Val Arg Tyr Tyr Arg Cys Ala Val Leu Ser
 1               5                  10                  15

Cys Leu Pro Lys Glu Glu Gln Ile Tyr Lys Cys Ser Thr Arg Tyr Arg
             20                  25                  30

Lys Cys Cys Arg Arg Lys Lys
         35

<210> SEQ ID NO 20
```

```
<211> LENGTH: 44
<212> TYPE: PRT
<213> ORGANISM: Artificial Sequence
<220> FEATURE:
<223> OTHER INFORMATION: Defensin polypeptide

<400> SEQUENCE: 20

Ile Ile Asn Thr Leu Gln Lys Tyr Tyr Cys Arg Val Arg Tyr Tyr Arg
 1               5                  10                  15

Cys Ala Val Leu Ser Cys Leu Pro Lys Glu Glu Gln Ile Tyr Lys Cys
            20                  25                  30

Ser Thr Arg Tyr Arg Lys Cys Cys Arg Arg Lys Lys
        35                  40

<210> SEQ ID NO 21
<211> LENGTH: 43
<212> TYPE: PRT
<213> ORGANISM: Artificial Sequence
<220> FEATURE:
<223> OTHER INFORMATION: Defensin polypeptide

<400> SEQUENCE: 21

Ile Ile Asn Thr Leu Gln Lys Tyr Tyr Cys Arg Val Arg Tyr Tyr Arg
 1               5                  10                  15

Cys Ala Val Leu Ser Cys Leu Pro Lys Glu Glu Gln Ile Tyr Lys Cys
            20                  25                  30

Ser Thr Arg Tyr Arg Lys Cys Cys Arg Arg Lys
        35                  40

<210> SEQ ID NO 22
<211> LENGTH: 42
<212> TYPE: PRT
<213> ORGANISM: Artificial Sequence
<220> FEATURE:
<223> OTHER INFORMATION: Defensin polypeptide

<400> SEQUENCE: 22

Ile Ile Asn Thr Leu Gln Lys Tyr Tyr Cys Arg Val Arg Tyr Tyr Arg
 1               5                  10                  15

Cys Ala Val Leu Ser Cys Leu Pro Lys Glu Glu Gln Ile Tyr Lys Cys
            20                  25                  30

Ser Thr Arg Tyr Arg Lys Cys Cys Arg Arg
        35                  40

<210> SEQ ID NO 23
<211> LENGTH: 43
<212> TYPE: PRT
<213> ORGANISM: Artificial Sequence
<220> FEATURE:
<223> OTHER INFORMATION: Defensin polypeptide

<400> SEQUENCE: 23

Ile Asn Thr Leu Gln Lys Tyr Tyr Cys Arg Val Arg Tyr Tyr Arg Cys
 1               5                  10                  15

Ala Val Leu Ser Cys Leu Pro Lys Glu Glu Gln Ile Tyr Lys Cys Ser
            20                  25                  30

Thr Arg Tyr Arg Lys Cys Cys Arg Arg Lys Lys
        35                  40

<210> SEQ ID NO 24
<211> LENGTH: 42
<212> TYPE: PRT
<213> ORGANISM: Artificial Sequence
```

<220> FEATURE:
<223> OTHER INFORMATION: Defensin polypeptide

<400> SEQUENCE: 24

Ile Asn Thr Leu Gln Lys Tyr Tyr Cys Arg Val Arg Tyr Tyr Arg Cys
1               5                   10                  15

Ala Val Leu Ser Cys Leu Pro Lys Glu Glu Gln Ile Tyr Lys Cys Ser
            20                  25                  30

Thr Arg Tyr Arg Lys Cys Cys Arg Arg Lys
        35                  40

<210> SEQ ID NO 25
<211> LENGTH: 41
<212> TYPE: PRT
<213> ORGANISM: Artificial Sequence
<220> FEATURE:
<223> OTHER INFORMATION: Defensin polypeptide

<400> SEQUENCE: 25

Ile Asn Thr Leu Gln Lys Tyr Tyr Cys Arg Val Arg Tyr Tyr Arg Cys
1               5                   10                  15

Ala Val Leu Ser Cys Leu Pro Lys Glu Glu Gln Ile Tyr Lys Cys Ser
            20                  25                  30

Thr Arg Tyr Arg Lys Cys Cys Arg Arg
        35                  40

<210> SEQ ID NO 26
<211> LENGTH: 42
<212> TYPE: PRT
<213> ORGANISM: Artificial Sequence
<220> FEATURE:
<223> OTHER INFORMATION: Defensin polypeptide

<400> SEQUENCE: 26

Asn Thr Leu Gln Lys Tyr Tyr Cys Arg Val Arg Tyr Tyr Arg Cys Ala
1               5                   10                  15

Val Leu Ser Cys Leu Pro Lys Glu Glu Gln Ile Tyr Lys Cys Ser Thr
            20                  25                  30

Arg Tyr Arg Lys Cys Cys Arg Arg Lys Lys
        35                  40

<210> SEQ ID NO 27
<211> LENGTH: 41
<212> TYPE: PRT
<213> ORGANISM: Artificial Sequence
<220> FEATURE:
<223> OTHER INFORMATION: Defensin polypeptide

<400> SEQUENCE: 27

Asn Thr Leu Gln Lys Tyr Tyr Cys Arg Val Arg Tyr Tyr Arg Cys Ala
1               5                   10                  15

Val Leu Ser Cys Leu Pro Lys Glu Glu Gln Ile Tyr Lys Cys Ser Thr
            20                  25                  30

Arg Tyr Arg Lys Cys Cys Arg Arg Lys
        35                  40

<210> SEQ ID NO 28
<211> LENGTH: 40
<212> TYPE: PRT
<213> ORGANISM: Artificial Sequence
<220> FEATURE:
<223> OTHER INFORMATION: Defensin polypeptide -continued

<400> SEQUENCE: 28

Asn Thr Leu Gln Lys Tyr Tyr Cys Arg Val Arg Tyr Tyr Arg Cys Ala
1               5                   10                  15
Val Leu Ser Cys Leu Pro Lys Glu Glu Gln Ile Tyr Lys Cys Ser Thr
            20                  25                  30
Arg Tyr Arg Lys Cys Cys Arg Arg
        35                  40

<210> SEQ ID NO 29
<211> LENGTH: 41
<212> TYPE: PRT
<213> ORGANISM: Artificial Sequence
<220> FEATURE:
<223> OTHER INFORMATION: Defensin polypeptide

<400> SEQUENCE: 29

Thr Leu Gln Lys Tyr Tyr Cys Arg Val Arg Tyr Tyr Arg Cys Ala Val
1               5                   10                  15
Leu Ser Cys Leu Pro Lys Glu Glu Gln Ile Tyr Lys Cys Ser Thr Arg
            20                  25                  30
Tyr Arg Lys Cys Cys Arg Arg Lys Lys
        35                  40

<210> SEQ ID NO 30
<211> LENGTH: 40
<212> TYPE: PRT
<213> ORGANISM: Artificial Sequence
<220> FEATURE:
<223> OTHER INFORMATION: Defensin polypeptide

<400> SEQUENCE: 30

Thr Leu Gln Lys Tyr Tyr Cys Arg Val Arg Tyr Tyr Arg Cys Ala Val
1               5                   10                  15
Leu Ser Cys Leu Pro Lys Glu Glu Gln Ile Tyr Lys Cys Ser Thr Arg
            20                  25                  30
Tyr Arg Lys Cys Cys Arg Arg Lys
        35                  40

<210> SEQ ID NO 31
<211> LENGTH: 39
<212> TYPE: PRT
<213> ORGANISM: Artificial Sequence
<220> FEATURE:
<223> OTHER INFORMATION: Defensin polypeptide

<400> SEQUENCE: 31

Thr Leu Gln Lys Tyr Tyr Cys Arg Val Arg Tyr Tyr Arg Cys Ala Val
1               5                   10                  15
Leu Ser Cys Leu Pro Lys Glu Glu Gln Ile Tyr Lys Cys Ser Thr Arg
            20                  25                  30
Tyr Arg Lys Cys Cys Arg Arg
        35

<210> SEQ ID NO 32
<211> LENGTH: 40
<212> TYPE: PRT
<213> ORGANISM: Artificial Sequence
<220> FEATURE:
<223> OTHER INFORMATION: Defensin polypeptide

<400> SEQUENCE: 32

Leu Gln Lys Tyr Tyr Cys Arg Val Arg Tyr Tyr Arg Cys Ala Val Leu

```
                  1               5                  10                 15
Ser Cys Leu Pro Lys Glu Glu Gln Ile Tyr Lys Cys Ser Thr Arg Tyr
                20                  25                 30

Arg Lys Cys Cys Arg Arg Lys Lys
            35                  40

<210> SEQ ID NO 33
<211> LENGTH: 39
<212> TYPE: PRT
<213> ORGANISM: Artificial Sequence
<220> FEATURE:
<223> OTHER INFORMATION: Defensin polypeptide

<400> SEQUENCE: 33

Leu Gln Lys Tyr Tyr Cys Arg Val Arg Tyr Tyr Arg Cys Ala Val Leu
 1               5                  10                 15

Ser Cys Leu Pro Lys Glu Glu Gln Ile Tyr Lys Cys Ser Thr Arg Tyr
                20                  25                 30

Arg Lys Cys Cys Arg Arg Lys
            35

<210> SEQ ID NO 34
<211> LENGTH: 38
<212> TYPE: PRT
<213> ORGANISM: Artificial Sequence
<220> FEATURE:
<223> OTHER INFORMATION: Defensin polypeptide

<400> SEQUENCE: 34

Leu Gln Lys Tyr Tyr Cys Arg Val Arg Tyr Tyr Arg Cys Ala Val Leu
 1               5                  10                 15

Ser Cys Leu Pro Lys Glu Glu Gln Ile Tyr Lys Cys Ser Thr Arg Tyr
                20                  25                 30

Arg Lys Cys Cys Arg Arg
            35

<210> SEQ ID NO 35
<211> LENGTH: 49
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (45)...(45)
<223> OTHER INFORMATION: leucine, isoleucine, valine, phenylalanine, or
      methionine

<400> SEQUENCE: 35

Pro Gly His Gly Gly Ile Ile Asn Thr Leu Gln Leu Tyr Tyr Cys Arg
 1               5                  10                 15

Val Arg Gly Gly Arg Cys Ala Val Leu Ser Cys Leu Pro Lys Glu Glu
                20                  25                 30

Cys Ile Gly Lys Met Ser Thr Arg Gly Arg Lys Cys Xaa Arg Arg Lys
            35                  40                 45

Lys

<210> SEQ ID NO 36
<211> LENGTH: 48
<212> TYPE: PRT
<213> ORGANISM: Artificial Sequence
<220> FEATURE:
<223> OTHER INFORMATION: Defensin polypeptide
```

```
<220> FEATURE:
<221> NAME/KEY: VARIANT
<222> LOCATION: (45)...(45)
<223> OTHER INFORMATION: leucine, isoleucine, valine, phenylalanine, or
      methionine

<400> SEQUENCE: 36

Pro Gly His Gly Gly Ile Ile Asn Thr Leu Gln Leu Tyr Tyr Cys Arg
 1               5                  10                  15

Val Arg Gly Gly Arg Cys Ala Val Leu Ser Cys Leu Pro Lys Glu Glu
            20                  25                  30

Cys Ile Gly Lys Met Ser Thr Arg Gly Arg Lys Cys Xaa Arg Arg Lys
        35                  40                  45

<210> SEQ ID NO 37
<211> LENGTH: 48
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (44)...(44)
<223> OTHER INFORMATION: leucine, isoleucine, valine, phenylalanine, or
      methionine

<400> SEQUENCE: 37

Gly His Gly Gly Ile Ile Asn Thr Leu Gln Leu Tyr Tyr Cys Arg Val
 1               5                  10                  15

Arg Gly Gly Arg Cys Ala Val Leu Ser Cys Leu Pro Lys Glu Glu Cys
            20                  25                  30

Ile Gly Lys Met Ser Thr Arg Gly Arg Lys Cys Xaa Arg Arg Lys Lys
        35                  40                  45

<210> SEQ ID NO 38
<211> LENGTH: 47
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (44)...(44)
<223> OTHER INFORMATION: leucine, isoleucine, valine, phenylalanine, or
      methionine

<400> SEQUENCE: 38

Gly His Gly Gly Ile Ile Asn Thr Leu Gln Leu Tyr Tyr Cys Arg Val
 1               5                  10                  15

Arg Gly Gly Arg Cys Ala Val Leu Ser Cys Leu Pro Lys Glu Glu Cys
            20                  25                  30

Ile Gly Lys Met Ser Thr Arg Gly Arg Lys Cys Xaa Arg Arg Lys
        35                  40                  45

<210> SEQ ID NO 39
<211> LENGTH: 47
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (43)...(43)
<223> OTHER INFORMATION: leucine, isoleucine, valine, phenylalanine, or
      methionine

<400> SEQUENCE: 39
```

His Gly Gly Ile Ile Asn Thr Leu Gln Leu Tyr Tyr Cys Arg Val Arg
1               5                   10                  15

Gly Gly Arg Cys Ala Val Leu Ser Cys Leu Pro Lys Glu Glu Cys Ile
            20                  25                  30

Gly Lys Met Ser Thr Arg Gly Arg Lys Cys Xaa Arg Arg Lys Lys
        35                  40                  45

<210> SEQ ID NO 40
<211> LENGTH: 46
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (43)...(43)
<223> OTHER INFORMATION: leucine, isoleucine, valine, phenylalanine, or
      methionine

<400> SEQUENCE: 40

His Gly Gly Ile Ile Asn Thr Leu Gln Leu Tyr Tyr Cys Arg Val Arg
1               5                   10                  15

Gly Gly Arg Cys Ala Val Leu Ser Cys Leu Pro Lys Glu Glu Cys Ile
            20                  25                  30

Gly Lys Met Ser Thr Arg Gly Arg Lys Cys Xaa Arg Arg Lys
        35                  40                  45

<210> SEQ ID NO 41
<211> LENGTH: 46
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (42)...(42)
<223> OTHER INFORMATION: leucine, isoleucine, valine, phenylalanine, or
      methionine

<400> SEQUENCE: 41

Gly Gly Ile Ile Asn Thr Leu Gln Leu Tyr Tyr Cys Arg Val Arg Gly
1               5                   10                  15

Gly Arg Cys Ala Val Leu Ser Cys Leu Pro Lys Glu Glu Cys Ile Gly
            20                  25                  30

Lys Met Ser Thr Arg Gly Arg Lys Cys Xaa Arg Arg Lys Lys
        35                  40                  45

<210> SEQ ID NO 42
<211> LENGTH: 45
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (42)...(42)
<223> OTHER INFORMATION: leucine, isoleucine, valine, phenylalanine, or
      methionine

<400> SEQUENCE: 42

Gly Gly Ile Ile Asn Thr Leu Gln Leu Tyr Tyr Cys Arg Val Arg Gly
1               5                   10                  15

Gly Arg Cys Ala Val Leu Ser Cys Leu Pro Lys Glu Glu Cys Ile Gly
            20                  25                  30

Lys Met Ser Thr Arg Gly Arg Lys Cys Xaa Arg Arg Lys
            35                  40                  45

<210> SEQ ID NO 43
<211> LENGTH: 45
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (41)...(41)
<223> OTHER INFORMATION: leucine, isoleucine, valine, phenylalanine, or
      methionine

<400> SEQUENCE: 43

Gly Ile Ile Asn Thr Leu Gln Leu Tyr Tyr Cys Arg Val Arg Gly Gly
 1               5                  10                  15

Arg Cys Ala Val Leu Ser Cys Leu Pro Lys Glu Glu Cys Ile Gly Lys
            20                  25                  30

Met Ser Thr Arg Gly Arg Lys Cys Xaa Arg Arg Lys Lys
            35                  40                  45

<210> SEQ ID NO 44
<211> LENGTH: 44
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (41)...(41)
<223> OTHER INFORMATION: leucine, isoleucine, valine, phenylalanine, or
      methionine

<400> SEQUENCE: 44

Gly Ile Ile Asn Thr Leu Gln Leu Tyr Tyr Cys Arg Val Arg Gly Gly
 1               5                  10                  15

Arg Cys Ala Val Leu Ser Cys Leu Pro Lys Glu Glu Cys Ile Gly Lys
            20                  25                  30

Met Ser Thr Arg Gly Arg Lys Cys Xaa Arg Arg Lys
            35                  40

<210> SEQ ID NO 45
<211> LENGTH: 44
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (40)...(40)
<223> OTHER INFORMATION: leucine, isoleucine, valine, phenylalanine, or
      methionine

<400> SEQUENCE: 45

Ile Ile Asn Thr Leu Gln Leu Tyr Tyr Cys Arg Val Arg Gly Gly Arg
 1               5                  10                  15

Cys Ala Val Leu Ser Cys Leu Pro Lys Glu Glu Cys Ile Gly Lys Met
            20                  25                  30

Ser Thr Arg Gly Arg Lys Cys Xaa Arg Arg Lys Lys
            35                  40

<210> SEQ ID NO 46
<211> LENGTH: 43
<212> TYPE: PRT

```
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (40)...(40)
<223> OTHER INFORMATION: leucine, isoleucine, valine, phenylalanine, or
      methionine

<400> SEQUENCE: 46

Ile Ile Asn Thr Leu Gln Leu Tyr Tyr Cys Arg Val Arg Gly Gly Arg
1               5                   10                  15

Cys Ala Val Leu Ser Cys Leu Pro Lys Glu Glu Cys Ile Gly Lys Met
            20                  25                  30

Ser Thr Arg Gly Arg Lys Cys Xaa Arg Arg Lys
        35                  40

<210> SEQ ID NO 47
<211> LENGTH: 43
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (39)...(39)
<223> OTHER INFORMATION: leucine, isoleucine, valine, phenylalanine, or
      methionine

<400> SEQUENCE: 47

Ile Asn Thr Leu Gln Leu Tyr Tyr Cys Arg Val Arg Gly Gly Arg Cys
1               5                   10                  15

Ala Val Leu Ser Cys Leu Pro Lys Glu Glu Cys Ile Gly Lys Met Ser
            20                  25                  30

Thr Arg Gly Arg Lys Cys Xaa Arg Arg Lys Lys
        35                  40

<210> SEQ ID NO 48
<211> LENGTH: 42
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (39)...(39)
<223> OTHER INFORMATION: leucine, isoleucine, valine, phenylalanine, or
      methionine

<400> SEQUENCE: 48

Ile Asn Thr Leu Gln Leu Tyr Tyr Cys Arg Val Arg Gly Gly Arg Cys
1               5                   10                  15

Ala Val Leu Ser Cys Leu Pro Lys Glu Glu Cys Ile Gly Lys Met Ser
            20                  25                  30

Thr Arg Gly Arg Lys Cys Xaa Arg Arg Lys
        35                  40

<210> SEQ ID NO 49
<211> LENGTH: 42
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (38)...(38)
<223> OTHER INFORMATION: leucine, isoleucine, valine, phenylalanine, or
```

-continued methionine

<400> SEQUENCE: 49

Asn Thr Leu Gln Leu Tyr Tyr Cys Arg Val Arg Gly Gly Arg Cys Ala
1               5                   10                  15

Val Leu Ser Cys Leu Pro Lys Glu Glu Cys Ile Gly Lys Met Ser Thr
            20                  25                  30

Arg Gly Arg Lys Cys Xaa Arg Arg Lys Lys
        35                  40

<210> SEQ ID NO 50
<211> LENGTH: 41
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (38)...(38)
<223> OTHER INFORMATION: leucine, isoleucine, valine, phenylalanine, or
      methionine

<400> SEQUENCE: 50

Asn Thr Leu Gln Leu Tyr Tyr Cys Arg Val Arg Gly Gly Arg Cys Ala
1               5                   10                  15

Val Leu Ser Cys Leu Pro Lys Glu Glu Cys Ile Gly Lys Met Ser Thr
            20                  25                  30

Arg Gly Arg Lys Cys Xaa Arg Arg Lys
        35                  40

<210> SEQ ID NO 51
<211> LENGTH: 41
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (37)...(37)
<223> OTHER INFORMATION: leucine, isoleucine, valine, phenylalanine, or
      methionine

<400> SEQUENCE: 51

Thr Leu Gln Leu Tyr Tyr Cys Arg Val Arg Gly Gly Arg Cys Ala Val
1               5                   10                  15

Leu Ser Cys Leu Pro Lys Glu Glu Cys Ile Gly Lys Met Ser Thr Arg
            20                  25                  30

Gly Arg Lys Cys Xaa Arg Arg Lys Lys
        35                  40

<210> SEQ ID NO 52
<211> LENGTH: 40
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (37)...(37)
<223> OTHER INFORMATION: leucine, isoleucine, valine, phenylalanine, or
      methionine

<400> SEQUENCE: 52

Thr Leu Gln Leu Tyr Tyr Cys Arg Val Arg Gly Gly Arg Cys Ala Val
1               5                   10                  15

```
Leu Ser Cys Leu Pro Lys Glu Glu Cys Ile Gly Lys Met Ser Thr Arg
            20                  25                  30

Gly Arg Lys Cys Xaa Arg Arg Lys
            35                  40
```

<210> SEQ ID NO 53
<211> LENGTH: 40
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (36)...(36)
<223> OTHER INFORMATION: leucine, isoleucine, valine, phenylalanine, or
      methionine

<400> SEQUENCE: 53

```
Leu Gln Leu Tyr Tyr Cys Arg Val Arg Gly Gly Arg Cys Ala Val Leu
  1               5                  10                  15

Ser Cys Leu Pro Lys Glu Glu Cys Ile Gly Lys Met Ser Thr Arg Gly
            20                  25                  30

Arg Lys Cys Xaa Arg Arg Lys Lys
            35                  40
```

<210> SEQ ID NO 54
<211> LENGTH: 39
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (36)...(36)
<223> OTHER INFORMATION: leucine, isoleucine, valine, phenylalanine, or
      methionine

<400> SEQUENCE: 54

```
Leu Gln Leu Tyr Tyr Cys Arg Val Arg Gly Gly Arg Cys Ala Val Leu
  1               5                  10                  15

Ser Cys Leu Pro Lys Glu Glu Cys Ile Gly Lys Met Ser Thr Arg Gly
            20                  25                  30

Arg Lys Cys Xaa Arg Arg Lys
            35
```

<210> SEQ ID NO 55
<211> LENGTH: 39
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (35)...(35)
<223> OTHER INFORMATION: leucine, isoleucine, valine, phenylalanine, or
      methionine

<400> SEQUENCE: 55

```
Gln Leu Tyr Tyr Cys Arg Val Arg Gly Gly Arg Cys Ala Val Leu Ser
  1               5                  10                  15

Cys Leu Pro Lys Glu Glu Cys Ile Gly Lys Met Ser Thr Arg Gly Arg
            20                  25                  30

Lys Cys Xaa Arg Arg Lys Lys
            35
```

<210> SEQ ID NO 56
<211> LENGTH: 38
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (35)...(35)
<223> OTHER INFORMATION: leucine, isoleucine, valine, phenylalanine, or methionine

<400> SEQUENCE: 56

```
Gln Leu Tyr Tyr Cys Arg Val Arg Gly Gly Arg Cys Ala Val Leu Ser
  1               5                  10                  15

Cys Leu Pro Lys Glu Glu Cys Ile Gly Lys Met Ser Thr Arg Gly Arg
             20                  25                  30

Lys Cys Xaa Arg Arg Lys
             35
```

<210> SEQ ID NO 57
<211> LENGTH: 38
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (34)...(34)
<223> OTHER INFORMATION: leucine, isoleucine, valine, phenylalanine, or methionine

<400> SEQUENCE: 57

```
Leu Tyr Tyr Cys Arg Val Arg Gly Gly Arg Cys Ala Val Leu Ser Cys
  1               5                  10                  15

Leu Pro Lys Glu Glu Cys Ile Gly Lys Met Ser Thr Arg Gly Arg Lys
             20                  25                  30

Cys Xaa Arg Arg Lys Lys
             35
```

<210> SEQ ID NO 58
<211> LENGTH: 37
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (34)...(34)
<223> OTHER INFORMATION: leucine, isoleucine, valine, phenylalanine, or methionine

<400> SEQUENCE: 58

```
Leu Tyr Tyr Cys Arg Val Arg Gly Gly Arg Cys Ala Val Leu Ser Cys
  1               5                  10                  15

Leu Pro Lys Glu Glu Cys Ile Gly Lys Met Ser Thr Arg Gly Arg Lys
             20                  25                  30

Cys Xaa Arg Arg Lys
         35
```

<210> SEQ ID NO 59
<211> LENGTH: 37
<212> TYPE: PRT
<213> ORGANISM: Artificial Sequence
<220> FEATURE:
<223> OTHER INFORMATION: Defensin polypeptide
<220> FEATURE:

```
<221> NAME/KEY: VARIANT
<222> LOCATION: (33)...(33)
<223> OTHER INFORMATION: leucine, isoleucine, valine, phenylalanine, or
      methionine

<400> SEQUENCE: 59

Tyr Tyr Cys Arg Val Arg Gly Gly Arg Cys Ala Val Leu Ser Cys Leu
1               5                   10                  15

Pro Lys Glu Glu Cys Ile Gly Lys Met Ser Thr Arg Gly Arg Lys Cys
            20                  25                  30

Xaa Arg Arg Lys Lys
        35

<210> SEQ ID NO 60
<211> LENGTH: 36
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (33)...(33)
<223> OTHER INFORMATION: leucine, isoleucine, valine, phenylalanine, or
      methionine

<400> SEQUENCE: 60

Tyr Tyr Cys Arg Val Arg Gly Gly Arg Cys Ala Val Leu Ser Cys Leu
1               5                   10                  15

Pro Lys Glu Glu Cys Ile Gly Lys Met Ser Thr Arg Gly Arg Lys Cys
            20                  25                  30

Xaa Arg Arg Lys
        35

<210> SEQ ID NO 61
<211> LENGTH: 36
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (32)...(32)
<223> OTHER INFORMATION: leucine, isoleucine, valine, phenylalanine, or
      methionine

<400> SEQUENCE: 61

Tyr Cys Arg Val Arg Gly Gly Arg Cys Ala Val Leu Ser Cys Leu Pro
1               5                   10                  15

Lys Glu Glu Cys Ile Gly Lys Met Ser Thr Arg Gly Arg Lys Cys Xaa
            20                  25                  30

Arg Arg Lys Lys
        35

<210> SEQ ID NO 62
<211> LENGTH: 35
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (32)...(32)
<223> OTHER INFORMATION: leucine, isoleucine, valine, phenylalanine, or
      methionine

<400> SEQUENCE: 62
```

```
Tyr Cys Arg Val Arg Gly Gly Arg Cys Ala Val Leu Ser Cys Leu Pro
 1               5                  10                  15

Lys Glu Glu Cys Ile Gly Lys Met Ser Thr Arg Gly Arg Lys Cys Xaa
            20                  25                  30

Arg Arg Lys
        35

<210> SEQ ID NO 63
<211> LENGTH: 35
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (31)...(31)
<223> OTHER INFORMATION: leucine, isoleucine, valine, phenylalanine, or
      methionine

<400> SEQUENCE: 63

Cys Arg Val Arg Gly Gly Arg Cys Ala Val Leu Ser Cys Leu Pro Lys
 1               5                  10                  15

Glu Glu Cys Ile Gly Lys Met Ser Thr Arg Gly Arg Lys Cys Xaa Arg
            20                  25                  30

Arg Lys Lys
        35

<210> SEQ ID NO 64
<211> LENGTH: 34
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (31)...(31)
<223> OTHER INFORMATION: leucine, isoleucine, valine, phenylalanine, or
      methionine

<400> SEQUENCE: 64

Cys Arg Val Arg Gly Gly Arg Cys Ala Val Leu Ser Cys Leu Pro Lys
 1               5                  10                  15

Glu Glu Cys Ile Gly Lys Met Ser Thr Arg Gly Arg Lys Cys Xaa Arg
            20                  25                  30

Arg Lys

<210> SEQ ID NO 65
<211> LENGTH: 34
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (30)...(30)
<223> OTHER INFORMATION: leucine, isoleucine, valine, phenylalanine, or
      methionine

<400> SEQUENCE: 65

Arg Val Arg Gly Gly Arg Cys Ala Val Leu Ser Cys Leu Pro Lys Glu
 1               5                  10                  15

Glu Cys Ile Gly Lys Met Ser Thr Arg Gly Arg Lys Cys Xaa Arg Arg
            20                  25                  30

Lys Lys
```

```
<210> SEQ ID NO 66
<211> LENGTH: 33
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (30)...(30)
<223> OTHER INFORMATION: leucine, isoleucine, valine, phenylalanine, or
      methionine

<400> SEQUENCE: 66

Arg Val Arg Gly Gly Arg Cys Ala Val Leu Ser Cys Leu Pro Lys Glu
1               5                   10                  15

Glu Cys Ile Gly Lys Met Ser Thr Arg Gly Arg Lys Cys Xaa Arg Arg
            20                  25                  30

Lys

<210> SEQ ID NO 67
<211> LENGTH: 33
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (29)...(29)
<223> OTHER INFORMATION: leucine, isoleucine, valine, phenylalanine, or
      methionine

<400> SEQUENCE: 67

Val Arg Gly Gly Arg Cys Ala Val Leu Ser Cys Leu Pro Lys Glu Glu
1               5                   10                  15

Cys Ile Gly Lys Met Ser Thr Arg Gly Arg Lys Cys Xaa Arg Arg Lys
            20                  25                  30

Lys

<210> SEQ ID NO 68
<211> LENGTH: 32
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (29)...(29)
<223> OTHER INFORMATION: leucine, isoleucine, valine, phenylalanine, or
      methionine

<400> SEQUENCE: 68

Val Arg Gly Gly Arg Cys Ala Val Leu Ser Cys Leu Pro Lys Glu Glu
1               5                   10                  15

Cys Ile Gly Lys Met Ser Thr Arg Gly Arg Lys Cys Xaa Arg Arg Lys
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (28)...(28)
<223> OTHER INFORMATION: leucine, isoleucine, valine, phenylalanine, or
      methionine
```

```
<400> SEQUENCE: 69

Arg Gly Gly Arg Cys Ala Val Leu Ser Cys Leu Pro Lys Glu Glu Cys
1               5                   10                  15

Ile Gly Lys Met Ser Thr Arg Gly Arg Lys Cys Xaa Arg Arg Lys Lys
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (28)...(28)
<223> OTHER INFORMATION: leucine, isoleucine, valine, phenylalanine, or
      methionine

<400> SEQUENCE: 70

Arg Gly Gly Arg Cys Ala Val Leu Ser Cys Leu Pro Lys Glu Glu Cys
1               5                   10                  15

Ile Gly Lys Met Ser Thr Arg Gly Arg Lys Cys Xaa Arg Arg Lys
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (27)...(27)
<223> OTHER INFORMATION: leucine, isoleucine, valine, phenylalanine, or
      methionine

<400> SEQUENCE: 71

Gly Gly Arg Cys Ala Val Leu Ser Cys Leu Pro Lys Glu Glu Cys Ile
1               5                   10                  15

Gly Lys Met Ser Thr Arg Gly Arg Lys Cys Xaa Arg Arg Lys Lys
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: Defensin polypeptide
<220> FEATURE:
<221> NAME/KEY: VARIANT
<222> LOCATION: (27)...(27)
<223> OTHER INFORMATION: leucine, isoleucine, valine, phenylalanine, or
      methionine

<400> SEQUENCE: 72

Gly Gly Arg Cys Ala Val Leu Ser Cys Leu Pro Lys Glu Glu Cys Ile
1               5                   10                  15

Gly Lys Met Ser Thr Arg Gly Arg Lys Cys Xaa Arg Arg Lys
            20                  25                  30
```